United States Patent
Greenlee et al.

(10) Patent No.: US 10,752,940 B2
(45) Date of Patent: Aug. 25, 2020

(54) COMPOUNDS AND METHODS FOR DETECTING OLIGONUCLEOTIDES

(71) Applicant: Ionis Pharmaceuticals, Inc., Carlsbad, CA (US)

(72) Inventors: Sarah Greenlee, San Diego, CA (US); Zhengrong Yu, Carlsbad, CA (US); Thazha P. Prakash, Carlsbad, CA (US); John E. Matson, Vista, CA (US)

(73) Assignee: Ionis Pharmaceuticals, Inc., Carlsbad, CA (US)

( * ) Notice: Subject to any disclaimer, the term of this patent is extended or adjusted under 35 U.S.C. 154(b) by 24 days.

(21) Appl. No.: 15/034,508

(22) PCT Filed: Nov. 10, 2014

(86) PCT No.: PCT/US2014/064874
§ 371 (c)(1),
(2) Date: May 4, 2016

(87) PCT Pub. No.: WO2015/070173
PCT Pub. Date: May 14, 2015

(65) Prior Publication Data
US 2016/0281148 A1 Sep. 29, 2016

Related U.S. Application Data

(60) Provisional application No. 61/902,112, filed on Nov. 8, 2013.

(51) Int. Cl.
C12Q 1/68 (2018.01)
C07H 21/00 (2006.01)
C12Q 1/6834 (2018.01)
C12Q 1/6837 (2018.01)
(Continued)

(52) U.S. Cl.
CPC ......... *C12Q 1/6834* (2013.01); *C12Q 1/6816* (2013.01); *C12Q 1/6825* (2013.01); *C12Q 1/6837* (2013.01)

(58) Field of Classification Search
CPC .................................. C12Q 1/68; C07H 21/00
See application file for complete search history.

(56) References Cited

U.S. PATENT DOCUMENTS 4,988,617 A * 1/1991 Landegren ........... C12Q 1/6827
435/6.11
5,484,909 A * 1/1996 Nietupski .............. C07H 21/00
435/252.9
5,679,519 A 10/1997 Oprandy
(Continued)

FOREIGN PATENT DOCUMENTS

WO WO 1998/002582 1/1998
WO WO 2008/101157 8/2008
WO WO 2009/067243 * 5/2009

OTHER PUBLICATIONS

Santra et al., Conjugation of Biomolecules with Luminophore-Doped Silica Nanoparticles for Photostable Biomarkers. Analytical Chemistry 73 :4988 (2001).*

(Continued)

*Primary Examiner* — Ethan C Whisenant
(74) *Attorney, Agent, or Firm* — McNeill Baur PLLC

(57) ABSTRACT

The present invention provides methods of detecting and/or quantitating a target oligonucleotide in a biological sample.

22 Claims, 1 Drawing Sheet
Specification includes a Sequence Listing.

(51) Int. Cl.
     *C12Q 1/6816*     (2018.01)
     *C12Q 1/6825*     (2018.01)

(56) References Cited

U.S. PATENT DOCUMENTS

| | | | | |
|---|---|---|---|---|
| 5,686,244 | A | 11/1997 | Gudibande et al. | |
| 5,759,773 | A * | 6/1998 | Tyagi | C12Q 1/6813 435/6.12 |
| 6,110,678 | A * | 8/2000 | Weisburg | C12Q 1/6813 435/6.12 |
| 6,410,231 | B1 * | 6/2002 | Arnold | C12Q 1/6827 435/6.1 |
| 7,399,845 | B2 | 7/2008 | Swayze et al. | |
| 8,163,477 | B2 | 4/2012 | Yu et al. | |
| 2001/0053519 | A1 * | 12/2001 | Fodor | B01J 19/0046 435/6.11 |
| 2002/0119475 | A1 * | 8/2002 | Ramberg | C07H 21/00 435/6.14 |
| 2002/0137060 | A1 * | 9/2002 | Brown-Augsburger | C12Q 1/6834 435/6.11 |
| 2003/0027184 | A1 * | 2/2003 | Gorenstein | C07H 21/00 435/6.11 |
| 2003/0194723 | A1 * | 10/2003 | Cunningham | C12Q 1/689 435/6.12 |
| 2004/0086892 | A1 * | 5/2004 | Crothers | C12Q 1/682 435/6.12 |
| 2005/0064469 | A1 * | 3/2005 | Schulz | G01N 33/54366 435/6.11 |
| 2005/0181430 | A1 * | 8/2005 | Kenten | C07H 21/00 435/6.11 |
| 2006/0030535 | A1 * | 2/2006 | Healy | C12N 15/115 514/44 R |
| 2007/0059735 | A1 * | 3/2007 | Cunningham | C12Q 1/689 435/6.15 |
| 2007/0178476 | A1 * | 8/2007 | Shima | C12Q 1/6816 435/6.11 |
| 2008/0241831 | A1 * | 10/2008 | Fan | C12Q 1/6844 435/6.16 |
| 2011/0183339 | A1 * | 7/2011 | Getman | C12Q 1/6893 435/6.12 |
| 2011/0308313 | A1 * | 12/2011 | Azimi | B01L 3/5027 73/335.04 |
| 2012/0058908 | A1 * | 3/2012 | Li | C12Q 1/6837 506/9 |
| 2012/0322064 | A1 * | 12/2012 | Alocilja | B82Y 15/00 435/6.11 |
| 2015/0322429 | A1 * | 11/2015 | Crooke | C12Q 1/6883 514/44 A |
| 2016/0068915 | A1 * | 3/2016 | Kennedy | C12Q 1/6886 506/2 |

OTHER PUBLICATIONS

Telser et al. DNA Oligomers and Duplexes Containing a Covalently Attached Derivative of Tris( 2,2'-bipyridine)ruthenium( 11): Synthesis and Characterization by Thermodynamic and Optical Spectroscopic Measurements. JACS 111 : 7221 (1989)).*
Benes et al., Expression profiling of microRNA using real-time quantitative PCR how to use it and what is available. Methods 50:244-249 (Year: 2010).*
Carthew et al., Origins and Mechanisms of miRNAs and siRNAs. Cell 136(4) :642655 (Year: 2009).*
Deiss et al., Multiplexed Sandwich Immunoassays Using Electrochemiluminescence Imaging Resolved at the Single Bead Level. JACS 131:6088-6089 (Year: 2009).*
The Glen Report vol. 20(2) Oct. (Year: 2008).*
Gui et al., Supersandwich-type electrochennilunninescenct aptasensor based on Ru(phen)3 2+ functionalized hollow gold nanoparticles as signal-amplifying tags. Biosensors and Bioelectronics 47 : 524-529 . Available on Apr. 6, 2013. (Year: 2013).*
Kauppinen et al., Detection of siRNA and miRNA. Methods in Molecular Biology 451 :217 (Year: 2008).*
Kilic et al., Electrochemical based detection of microRNA, mir21 in breast cancer cells. Biosensors and Bioelctronics 38 :195-201 (Year: 2012).*
Liu et al., Rapid and reliable microRNA detection by stacking hybridization on electrochemiluminescent chip system. Biosensors and Bioelctronics 38 :195-201 (Year: 2014).*
Liu et al., "Off-On" Electrochemiluminescence System for Sensitive Detection of ATP via Target-Induced Structure Switching. Analytical Chemistry 86 : 8715-8741. (Year: 2014).*
Manoharan, M., RNA interference and chemically modified small interfering RNAs. Current Opinions in Chemical Biology 8 :570-579 (Year: 2004).*
McManus et al., Gene Silencing in Mammals by Small Interfering RNASs. Nature Reviews| Genetics 3 :737 (Year: 2002).*
Miao, W., Electrogenerated Chemiluminescence and Its Biorelated Applications. Chem. Rev. 1'098 : 2506-2553 (Year: 2008).*
Peng et al., A highly sensitive microRNA biosensor based on ruthenium oxide nanoparticle-initiated polymerization of aniline. Chem. Commun. 48 :9131-9133 (Year: 2010).*
Pohlmann et al., Electrochemical Detection of Micro RNAs via Gap Hybridization Assay. Analytical Chemistry 82 :4434-4440 (Year: 2010).*
Tu et al., Fluorescence quenching of gold nanoparticles integrating with a conformation-switched hairpin oligonucleotide probe for microRNA detection. Chem. Commun. 48 : 10718-10720 (Year: 2012).*
Qian et al., Analytica Chimica Acta 665 : 32-38 (Year: 2010).*
Sakata et al., Langmuir 23(5) : 2269 (Year: 2007).*
Yin et al., Electrochemical determination of microRNA-21 based on graphene, LNA integrated molecular beacon, AuNPs and biotin multifunctional bio bar codes and enzymatic assay system. Biosensors and Bioelectronics 33 : 247 (Year: 2012).*
Brown-Augsburger et al., "Development and validation of a sensitive, specific, and rapid hybridization-ELISA assay for determination of concentrations of a ribozyme in biological matrices." J Pharm Biomed Anal. (2004) 34(1):129-139.
Chan et al., "A Novel Ultrasensitive Hybridization-Based ELISA Method for 2-Methoxyphosphorothiolate MicroRNAs and Its In vitro and In vivo Application" AAPS J. (2010) 12(4):556-568.
Dai et al., "Cellular Uptake and Intracellular Levels of the Bcl-2 Antisense G3139 in Cultured Cells and Treated Patients with Acute Myeloid Leukemia" Clin Cancer Res. (2005) 11(8):2998-3008.
Deverre et al., "A competitive enzyme hybridization assay for plasma determination of phosphodiester and phosphorothioate antisense oligonucleotides." (1997) Nucleic Acids Res. 25(18):3584-3589.
Efler et al., "Quantification of oligodeoxynucteotides in human plasma with a novel hybridization assay offers greatly enhanced sensitivity over capillary gel electrophoresis." Oligonucleotides (2005) 15(2):119-131.
Freier et al., "The ups and downs of nucleic acid duplex stability: structure-stability studies on chemically-modified DNA:RNA duplexes" Nucleic Acids Research (1997) 25(22): 4429-4443.
Geary et al., "Pharmacokinetics of a tumor necrosis factor-alpha phosphorothioate 2'-O-(2-methoxyethyl) modified antisense oligonucleotide: comparison across species." Drug Metab Dispos. (2003) 31:1419-1428.
Geary et al., "Antisense oligonucleotide pharmacokinetics and metabolism." Expert Opin Drug Metab Toxicol. (2009) 5(4): 381-391.
Greenlee et al., "Development of a Hybridization method Coupled with MSD Electrochemiluminecence (ECL) Detection for Highly Sensitive Quantification of Second-Generation Antisense Oligonucleotides (ASOs)," Poser Presentation, AAPS Annual Meeting, Nov. 14, 2013.
International Search Report for application PCT/US2014/064874 dated Feb. 20, 2015.
Lakowicz et al., Development of Long-Lifetime Metal-Ligand Probes for Biophysics and Cellular Imaging.: J. of Fluorescence (1997) 7:17-25.

(56) References Cited

OTHER PUBLICATIONS

Sewell et al., "Phase I trial of ISIS 104838, a 2'-methoxyethyl modified antisense oligonucleotide targeting tumor necrosis factor-alpha." J Pharmacol Exp Ther (2002) 303:1334-1343.

Terpetschnig et al., "Metal-Ligand Complexes as a New Class of Long-Lived Fluorophomes for Protein Hydrodynamics." Biophys J. (1995) 68:342-350.

Tremblay et al., "Dual ligation hybridization assay for the specific determination of oligonucleotide therapeutics." Bioanalysis (2011) 3(5):499-508.

Wei et al., "A specific picomolar hybridization-based ELISA assay for the determination of phosphorothioate oligonucleotides in plasma and cellular matrices." Pharm. Res. (2006) 23:1251-1264.

Yu et al., "A Decade of Isis Experience with Hybridization Based ELISA (HELISA) Methods for Quantitation of Antisense Oligonucleotides in Biological Matrices" Oral Presentation, APA Meeting, Sep. 17, 2012.

Yu et al., "Development of an ultrasensitive noncompetitive hybridization-ligation enzyme-linked immunosorbent assay for the determination of phosphorothioate oligodeoxynucleotide in plasma." Anal Biochem (2002) 304(1):19-25.

Zhou et al., "Rapid and sensitive detection of point mutation by DNA ligase-based electrochemiluminescense assay." Talanta (2009) 78:1253-1528.

Bae et al., "Highly sensitive detection of DNA by electrogenerated chemiluminescence amplification using dendritic Ru(bpy)(3)(2+)-doped silica nanoparticles" (2010) 135(3): 603-607.

Extended European Search Report for Application No. 14860026.5 dated May 17, 2017.

Li et al., "Ultrasensitive electrogenerated chemiluminescence detection of DNA hybridization using carbon-nanotubes loaded with tris(2,2'-bipyridyl) ruthenium derivative tags" (2007) 72(5): 1704-1709.

Seth et al., "Design, synthesis and evaluation of constrained methoxyethyl (cMOE) and constrained ethyl (cEt) nucleoside analogs" (2008) 52: 553-554.

Tremblay et al., "Bioanalysis of siRNA and oligonucleotide therapeutics in biological fluids and tissues" (2009) 1(3): 595-609.

* cited by examiner

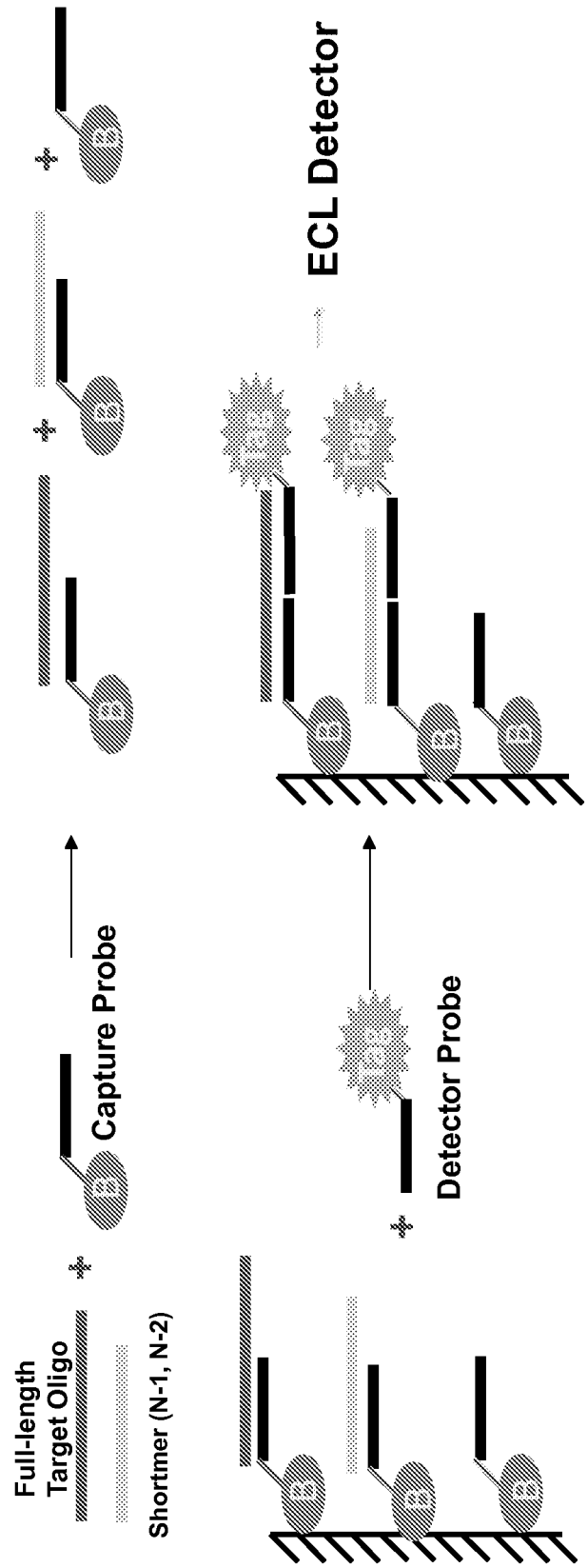

SEQUENCE LISTING

<160> NUMBER OF SEQ ID NOS: 8

<210> SEQ ID NO 1

```
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 1
tcactttcat aatgctgg                                                   18

<210> SEQ ID NO 2
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 2 ccagcatta                                                              9

<210> SEQ ID NO 3
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 3 tgaaagtga                                                              9

<210> SEQ ID NO 4
<211> LENGTH: 14
<212> TYPE: DNA
<213> ORGANISM: Artificial Sequence
<220> FEATURE:
<223> OTHER INFORMATION: Synthetic oligonucleotide

<400> SEQUENCE: 4
tcagtcatga cttc                                                       14

<210> SEQ ID NO 5
<211> LENGTH: 7
<212> TYPE: DNA
<213> ORGANISM: Artificial Sequence
<220> FEATURE:
<223> OTHER INFORMATION: Synthetic oligonucleotide

<400> SEQUENCE: 5 gaagtca                                                                7

<210> SEQ ID NO 6
<211> LENGTH: 7
<212> TYPE: DNA
<213> ORGANISM: Artificial Sequence
<220> FEATURE:
<223> OTHER INFORMATION: Synthetic oligonucleotide

<400> SEQUENCE: 6 tgactga                                                                7

<210> SEQ ID NO 7
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 7
```

```
ggttcccgag gtgccca                                                  17

<210> SEQ ID NO 8
<211> LENGTH: 8
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (3)..(3)
<223> OTHER INFORMATION: n = inosine

<400> SEQUENCE: 8 tgngcacc                                                            8
```

COMPOUNDS AND METHODS FOR DETECTING OLIGONUCLEOTIDES

SEQUENCE LISTING

The present application is being filed along with a Sequence Listing in electronic format. The Sequence Listing is provided as a file entitled CORE0121USASEQ_ST25.txt, created May 4, 2016, which is 4 Kb in size. The information in the electronic format of the sequence listing is incorporated herein by reference in its entirety.

BACKGROUND OF THE INVENTION

Oligonucleotides, such as aptamers and antisense oligonucleotides have been used therapeutically. Oligonucleotides comprising a variety of chemical modifications and motifs have been described. In certain instances, such oligonucleotides are useful as research tools, diagnostic reagents, and as therapeutic agents. Certain antisense oligonucleotides comprising at least a region of DNA-like nucleosides have been shown to reduce protein expression. Certain such antisense oligonucleotides act at least partially through RNase H. Certain RNA-like antisense oligonucleotides are known to inhibit protein expression in cells. Such RNA-like oligonucleotides function, at least in part, through the RNA-inducing silencing complex (RISC). Antisense oligonucleotides may be single-stranded or double-stranded. Antisense oligonucleotides have also been shown to alter processing of pre-mRNA and to modulate non-coding RNA molecules. In certain instances antisense oligonucleotides have been shown to modulate protein expression by binding to a target messenger RNA (mRNA) encoding the protein. In certain instances, such binding of an antisense oligonucleotides to its target mRNA results in cleavage of the mRNA. Antisense oligonucleotides that modulate processing of a pre-mRNA have also been reported. Such antisense oligonucleotides alter splicing, interfere with polyadenlyation or prevent formation of the 5'-cap of a pre-mRNA.

Therapeutic oligonucleotides may be administered to an animal. In certain instances it is desired to detect or quantify the amount of therapeutic oligonucleotides in a biological sample from an animal to which a compound has been administered. Certain assays for such purposes have been reported. See for example U.S. Pat. No. 8,163,477. The present disclosure describes compounds and methods that have improved sensitivity, ease of use, and/or reduced cost compared to previously described assays.

SUMMARY OF THE INVENTION

The present disclosure provides compounds and methods for detecting and quantifying one or more target oligonucleotides in a biological sample. In certain embodiments, such compounds and methods are highly sensitive, easy to perform, and/or inexpensive.

The present disclosure provides the following non-limiting numbered embodiments:

Embodiment 1

A method for detecting or quantitating a target oligonucleotide in a bodily fluid or extract wherein the target oligonucleotide is 8 to 50 nucleosides in length, comprising:
creating a test sample by contacting the bodily fluid or extract with a capture probe, wherein:
the capture probe is complementary to a first portion of the target oligonucleotide; and
the capture probe comprises a binding moiety, wherein the binding moiety is covalently bound to the capture probe;
contacting the test sample with a solid support wherein the solid support comprises a binding partner of the binding moiety of the capture probe;
contacting the test sample with a detector probe, wherein:
the detector probe is complementary to a second portion of the target oligonucleotide,
wherein the first portion and the second portion of the target oligonucleotide do not overlap; and
the detector probe comprises a electrochemiluminescent moiety, wherein the electrochemiluminescent moiety is covalently bound to the detector probe;
washing the test sample to remove unbound probe;
detecting the presence or amount of the electrochemiluminescent moiety in the test sample; and
thereby detecting or quantitating the target oligonucleotide in the bodily fluid or extract.

Embodiment 2

The method of embodiment 1, wherein the target oligonucleotide is 10-40 nucleosides in length.

Embodiment 3

The method of embodiment 1, wherein the target oligonucleotide is 14-40 nucleosides in length.

Embodiment 4

The method of embodiment 1, wherein the target oligonucleotide is 18-40 nucleosides in length.

Embodiment 5

The method of embodiment 1, wherein the target oligonucleotide is 20-40 nucleosides in length.

Embodiment 6

The method of embodiment 1, wherein the target oligonucleotide is 10-30 nucleosides in length.

Embodiment 7

The method of embodiment 1, wherein the target oligonucleotide is 14-30 nucleosides in length.

Embodiment 8

The method of embodiment 1, wherein the target oligonucleotide is 18-30 nucleosides in length.

Embodiment 9

The method of embodiment 1, wherein the target oligonucleotide is 20-30 nucleosides in length.

Embodiment 10

The method of embodiment 1, wherein the target oligonucleotide is 10-22 nucleosides in length.

Embodiment 11

The method of embodiment 1, wherein the target oligonucleotide is 14-22 nucleosides in length.

Embodiment 12

The method of embodiment 1, wherein the target oligonucleotide is 18-22 nucleosides in length.

Embodiment 13

The method of embodiment 1, wherein the target oligonucleotide is 20-22 nucleosides in length.

Embodiment 14

The method of any of embodiments 1-13 wherein the target oligonucleotide comprises at least modified nucleoside.

Embodiment 15

The method of embodiment 14 wherein the target oligonucleotide comprises at least one modified nucleoside comprising a 2'-O-methoxyethyl modification.

Embodiment 16

The method of embodiment 14 or 15, wherein the target oligonucleotide comprises at least one bicyclic nucleoside.

Embodiment 17

The method of embodiment 16 wherein the target oligonucleotide comprises at least one cEt nucleoside.

Embodiment 18

The method of any of embodiments 14-17 wherein the target oligonucleotide is a gapmer.

Embodiment 19

The method of any of embodiments 14-17 wherein the target oligonucleotide is a hemimer.

Embodiment 20

The method of any of embodiments 1-19 wherein the target oligonucleotide comprises at least one modified base.

Embodiment 21

The method of any of embodiments 1-20 wherein the target oligonucleotide comprises at least one modified internucleoside linkage.

Embodiment 22

The method of any of embodiments 1-21 wherein the target oligonucleotide is an aptamer.

Embodiment 23

The method of any of embodiments 1-21, wherein the target oligonucleotide is an antisense oligonucleotide.

Embodiment 24

The method of embodiment 23, wherein the target oligonucleotide is an RNase H dependent antisense compound.

Embodiment 25

The method of embodiment 24, wherein the target oligonucleotide is a RISC dependent antisense compound.

Embodiment 26

The method of any of embodiments 1-25, wherein the target olignucleotide is single-stranded.

Embodiment 27

The method of any of embodiments 1-26, wherein the target olignucleotide is double-stranded.

Embodiment 28

The method of any of embodiments 1-27, wherein the target oligonucleotide is self-structured under physiologic conditions.

Embodiment 29

The method of any of embodiments 1-28 wherein the bodily fluid is plasma.

Embodiment 30

The method of any of embodiments 1-28 wherein the bodily fluid is cerebral-spinal fluid.

Embodiment 31

The method of any of embodiments 1-30 wherein the binding moiety of the capture probe is conjugated to the 5' end of the capture probe.

Embodiment 32

The method of any of embodiments 1-30 wherein the binding moiety of the capture probe is conjugated to the 3' end of the capture probe.

Embodiment 33

The method of any of embodiments 1-32 wherein the capture probe comprises at least one 2'-O-methoxyethyl sugar modification.

Embodiment 34

The method of any of embodiments 1-33 wherein the capture probe comprises at least one cEt sugar modification.

Embodiment 35

The method of any of embodiments 1-34 wherein the capture probe comprises at least one 2'-F sugar modification.

Embodiment 36

The method of any of embodiments 1-35 wherein the capture probe comprises at least one 2'-deoxy sugar.

Embodiment 37

The method of any of embodiments 1-36 wherein the capture probe comprises at least one inosine.

Embodiment 38

The method of any of embodiments 1-37 wherein the detector probe comprises at least one 2'-O-methoxyethyl sugar modification.

Embodiment 39

The method of any of embodiments 1-38 wherein the detector probe comprises at least one cEt sugar modification.

Embodiment 40

The method of any of embodiments 1-39 wherein the detector probe comprises at least one 2'-F sugar modification.

Embodiment 41

The method of any of embodiments 1-40 wherein the detector probe comprises at least one 2'-deoxy sugar.

Embodiment 42

The method of any of embodiments 1-41 wherein the detector probe comprises at least one inosine.

Embodiment 43

The method of any of embodiments 1-42 wherein the electrochemiluminescent moiety of the detector probe is conjugated to the 3' end of the detector probe.

Embodiment 44

The method of any of embodiments 1-42 wherein the electrochemiluminescent moiety of the detector probe is conjugated to the 5' end of the detector probe.

Embodiment 45

The method of any of embodiments 1-18 wherein the capture and detector probes are each 7-10 nucleotides in length.

Embodiment 46

The method of any of embodiments 1-45 wherein detecting the electrochemiluminescent moiety is a tris(2,2-bipyridine) Ruthenium (II) tag.

Embodiment 47

The method of any of embodiments 1-46 wherein the method does not comprise addition of a ligase.

Embodiment 48

The method of any of embodiments 1-47 wherein the method does not comprise addition of a nuclease.

Embodiment 49

The method of any of embodiments 1-48 wherein the method has a sensitivity of less than 1 ng/ml of target oligonucleotide.

Embodiment 50

The method of any of embodiments 1-48 wherein the method has a sensitivity of less than 500 pg/ml of target oligonucleotide.

Embodiment 51

The method of any of embodiments 1-48 wherein the method has a sensitivity of less than 100 pg/ml of target oligonucleotide.

Embodiment 52

The method of any of embodiments 1-48 wherein the method has a sensitivity of less than 50 pg/ml of target oligonucleotide.

Embodiment 53

The method of any of embodiments 1-48 wherein the method has a sensitivity of less than 10 pg/ml of target oligonucleotide.

Embodiment 54

The method of any of embodiments 1-53, wherein the method is performed using less than 100 µl of biological fluid or extract.

Embodiment 55

The method of any of embodiments 1-53, wherein the method is performed using less than 75 µl of biological fluid or extract.

Embodiment 56

The method of any of embodiments 1-53, wherein the method is performed using less than 50 µl of biological fluid or extract.

Embodiment 57

The method of any of embodiments 1-53, wherein the method is performed using less than 30 µl of biological fluid or extract.

Embodiment 58

The method of any of embodiments 1-53, wherein the method is performed using 25 µl of biological fluid or extract.

Embodiment 59

The method of any of embodiments 1-58 comprising administering the target oligonucleotide to an animal and collecting the bodily fluid or extract.

Embodiment 60

The method of any of embodiments 1-59 wherein the contacting of the test sample with the capture probe is done prior to contacting of the test sample with the detector probe.

Embodiment 61

The method of any of embodiments 1-60 wherein the contacting of the test sample with the capture probe is done after contacting of the test sample with the detector probe.

Embodiment 62

The method of any of embodiments 1-61 wherein the solid support is first incubated with blocking solution to reduce non-specific binding of the probes and test sample components to the solid support.

Embodiment 63

The method of embodiment 62 wherein the solid support is washed following the blocking solution incubation.

Embodiment 64

The method of any of embodiments 1-63 wherein the detector probe is heated prior to contacting the test sample with the detector probe.

Embodiment 65

The method of any of embodiments 1-64 wherein the solid support is washed following each probe addition to the solid support.

Embodiment 66

The method of any of embodiments 1-65 further comprising contacting the test sample with a protease.

Embodiment 67

The method of embodiment 66 wherein the protease is Proteinase K.

Embodiment 68

The method of any of embodiments 66 or 67 wherein the contacting of the test sample with the protease is done prior to contacting the test sample with the detector probe.

Embodiment 69

The method of any of embodiments 66-68 wherein the contacting of the test sample with the protease is done at the same as the contacting of the test sample with the capture probe.

BRIEF DESCRIPTION OF THE FIGURES

FIG. 1 depicts a schematic summary of the dual probe ECL detection method.

DETAILED DESCRIPTION OF THE INVENTION

Unless specific definitions are provided, the nomenclature used in connection with, and the procedures and techniques of, analytical chemistry, synthetic organic chemistry, and medicinal and pharmaceutical chemistry described herein are those well known and commonly used in the art. Standard techniques may be used for chemical synthesis, and chemical analysis. Certain such techniques and procedures may be found for example in "Carbohydrate Modifications in Antisense Research" Edited by Sangvi and Cook, American Chemical Society, Washington D.C., 1994; "Remington's Pharmaceutical Sciences," Mack Publishing Co., Easton, Pa., $21^{st}$ edition, 2005; and "Antisense Drug Technology, Principles, Strategies, and Applications" Edited by Stanley T. Crooke, CRC Press, Boca Raton, Fla.; and Sambrook et al., "Molecular Cloning, A laboratory Manual," $2^{nd}$ Edition, Cold Spring Harbor Laboratory Press, 1989, which are hereby incorporated by reference for any purpose. Where permitted, all patents, applications, published applications and other publications and other data referred to throughout in the disclosure are incorporated by reference herein in their entirety.

Unless otherwise indicated, the following terms have the following meanings:

As used herein, "chemical modification" means a chemical difference in a compound when compared to a reference compound. In certain contexts, a chemical modification is a chemical difference when compared to a naturally occurring counterpart. In reference to an oligonucleotide, chemical modification does not include differences only in nucleobase sequence. Chemical modifications of oligonucleotides include nucleoside modifications (including sugar moiety modifications and nucleobase modifications) and internucleoside linkage modifications.

As used herein, "furanosyl" means a structure comprising a 5-membered ring comprising four carbon atoms and one oxygen atom.

As used herein, "naturally occurring sugar moiety" means a ribofuranosyl as found in naturally occurring RNA or a deoxyribofuranosyl as found in naturally occurring DNA.

As used herein, "sugar moiety" means a naturally occurring sugar moiety or a modified sugar moiety of a nucleoside.

As used herein, "modified sugar moiety" means a substituted sugar moiety, a bicyclic or tricyclic sugar moiety, or a sugar surrogate.

As used herein, "substituted sugar moiety" means a furanosyl comprising at least one substituent group that differs from that of a naturally occurring sugar moiety. Substituted sugar moieties include, but are not limited to furanosyls comprising substituents at the 2'-position, the 3'-position, the 5'-position and/or the 4'-position.

As used herein, "2'-substituted sugar moiety" means a furanosyl comprising a substituent at the 2'-position other than H or OH. Unless otherwise indicated, a 2'-substituted sugar moiety is not a bicyclic sugar moiety (i.e., the 2'-substituent of a 2'-substituted sugar moiety does not form a bridge to another atom of the furanosyl ring.

As used herein, "MOE" means —$OCH_2CH_2OCH_3$.

As used herein, "bicyclic sugar moiety" means a modified sugar moiety comprising a 4 to 7 membered ring (including but not limited to a furanosyl) comprising a bridge connecting two atoms of the 4 to 7 membered ring to form a second ring, resulting in a bicyclic structure. In certain embodiments, the 4 to 7 membered ring is a sugar ring. In certain embodiments the 4 to 7 membered ring is a furanosyl. In certain such embodiments, the bridge connects the 2'-carbon and the 4'-carbon of the furanosyl.

As used herein the term "sugar surrogate" means a structure that does not comprise a furanosyl and that is capable of replacing the naturally occurring sugar moiety of a nucleoside, such that the resulting nucleoside is capable of (1) incorporation into an oligonucleotide and (2) hybridization to a complementary nucleoside. Such structures include rings comprising a different number of atoms than furanosyl (e.g., 4, 6, or 7-membered rings); replacement of the oxygen of a furanosyl with a non-oxygen atom (e.g., carbon, sulfur, or nitrogen); or both a change in the number of atoms and a replacement of the oxygen. Such structures may also comprise substitutions corresponding to those described for substituted sugar moieties (e.g., 6-membered carbocyclic bicyclic sugar surrogates optionally comprising additional substituents). Sugar surrogates also include more complex sugar replacements (e.g., the non-ring systems of peptide nucleic acid). Sugar surrogates include without limitation morpholino, modified morpholinos, cyclohexenyls and cyclohexitols.

As used herein, "nucleotide" means a nucleoside further comprising a phosphate linking group. As used herein, "linked nucleosides" may or may not be linked by phosphate linkages and thus includes, but is not limited to "linked nucleotides." As used herein, "linked nucleosides" are nucleosides that are connected in a continuous sequence (i.e. no additional nucleosides are present between those that are linked).

As used herein, "nucleobase" means a group of atoms that can be linked to a sugar moiety to create a nucleoside that is capable of incorporation into an oligonucleotide, and wherein the group of atoms is capable of bonding with a complementary naturally occurring nucleobase of another oligonucleotide or nucleic acid. Nucleobases may be naturally occurring or may be modified.

As used herein, "heterocyclic base" or "heterocyclic nucleobase" means a nucleobase comprising a heterocyclic structure.

As used herein the terms, "unmodified nucleobase" or "naturally occurring nucleobase" means the naturally occurring heterocyclic nucleobases of RNA or DNA: the purine bases adenine (A) and guanine (G), and the pyrimidine bases thymine (T), cytosine (C) (including 5-methyl C), and uracil (U).

As used herein, "modified nucleobase" means any nucleobase that is not a naturally occurring nucleobase.

As used herein, "modified nucleoside" means a nucleoside comprising at least one chemical modification compared to naturally occurring RNA or DNA nucleosides. Modified nucleosides comprise a modified sugar moiety and/or a modified nucleobase.

As used herein, "bicyclic nucleoside" or "BNA" means a nucleoside comprising a bicyclic sugar moiety.

As used herein, "constrained ethyl nucleoside" or "cEt" means a nucleoside comprising a bicyclic sugar moiety comprising a 4'-CH(CH$_3$)—O-2'bridge.

As used herein, "locked nucleic acid nucleoside" or "LNA" means a nucleoside comprising a bicyclic sugar moiety comprising a 4'-CH$_2$—O-2'bridge.

As used herein, "2'-substituted nucleoside" means a nucleoside comprising a substituent at the 2'-position other than H or OH. Unless otherwise indicated, a 2'-substituted nucleoside is not a bicyclic nucleoside.

As used herein, "2'-deoxynucleoside" means a nucleoside comprising 2'-H furanosyl sugar moiety, as found in naturally occurring deoxyribonucleosides (DNA). In certain embodiments, a 2'-deoxynucleoside may comprise a modified nucleobase or may comprise an RNA nucleobase (e.g., uracil).

As used herein, "oligonucleotide" means a compound comprising a plurality of linked nucleosides. In certain embodiments, an oligonucleotide comprises one or more unmodified ribonucleosides (RNA) and/or unmodified deoxyribonucleosides (DNA) and/or one or more modified nucleosides.

As used herein "oligonucleoside" means an oligonucleotide in which none of the internucleoside linkages contains a phosphorus atom. As used herein, oligonucleotides include oligonucleosides.

As used herein, "modified oligonucleotide" means an oligonucleotide comprising at least one modified nucleoside and/or at least one modified internucleoside linkage.

As used herein "internucleoside linkage" means a covalent linkage between adjacent nucleosides in an oligonucleotide.

As used herein "naturally occurring internucleoside linkage" means a 3' to 5' phosphodiester linkage.

As used herein, "modified internucleoside linkage" means any internucleoside linkage other than a naturally occurring internucleoside linkage.

As used herein, "oligomeric compound" means a polymeric structure comprising two or more sub-structures. In certain embodiments, an oligomeric compound comprises an oligonucleotide. In certain embodiments, an oligomeric compound comprises one or more conjugate groups and/or terminal groups. In certain embodiments, an oligomeric compound consists of an oligonucleotide.

As used herein, "terminal group" means one or more atom attached to either, or both, the 3' end or the 5' end of an oligonucleotide. In certain embodiments a terminal group is a conjugate group. In certain embodiments, a terminal group comprises one or more terminal group nucleosides.

As used herein, "conjugate" means an atom or group of atoms bound to an oligonucleotide or oligomeric compound. In general, conjugate groups modify one or more properties of the compound to which they are attached, including, but not limited to pharmacodynamic, pharmacokinetic, binding, absorption, cellular distribution, cellular uptake, charge and/or clearance properties.

As used herein, "conjugate linking group" means any atom or group of atoms used to attach a conjugate to an oligonucleotide or oligomeric compound.

As used herein, "antisense compound" means a compound comprising or consisting of an oligonucleotide at least a portion of which is complementary to a target nucleic acid to which it is capable of hybridizing, resulting in at least one antisense activity.

As used herein, "antisense activity" means any detectable and/or measurable change attributable to the hybridization of an antisense compound to its target nucleic acid.

As used herein, "detecting" or "measuring" means that a test or assay for detecting or measuring is performed. Such detection and/or measuring may result in a value of zero. Thus, if a test for detection or measuring results in a finding of no activity (activity of zero), the step of detecting or measuring the activity has nevertheless been performed.

As used herein, "detectable and/or measurable activity" means a statistically significant activity that is not zero.

As used herein, "electrochemiluminescent tag" or "ECL tag" means an electrochemiluminescent luminophore that emits light following excitation and is conjugated to a molecule. In certain embodiments, the molecule is an oligonucleotide. In certain embodiments, an ECL tag comprises a metal-ligand complex. In certain embodiments, the metal-ligand complex is a tris(2,2-bipyridine) Ruthenium (II) complex.

As used herein, "binding moiety" means a chemical structure that binds specifically to a partner chemical structure. Examples of binding moieties and their partner structures include but are not limited to biotin-streptavidin, antigen-antibody partners, and FKBP12-Rapamycin.

As used herein, "essentially unchanged" means little or no change in a particular parameter, particularly relative to another parameter which changes much more. In certain embodiments, a parameter is essentially unchanged when it changes less than 5%. In certain embodiments, a parameter is essentially unchanged if it changes less than two-fold while another parameter changes at least ten-fold. For example, in certain embodiments, an antisense activity is a change in the amount of a target nucleic acid. In certain such embodiments, the amount of a non-target nucleic acid is essentially unchanged if it changes much less than the target nucleic acid does, but the change need not be zero.

As used herein, "nucleobase complementarity" or "complementarity" when in reference to nucleobases means a nucleobase that is capable of base pairing with another nucleobase. For example, in DNA, adenine (A) is complementary to thymine (T). For example, in RNA, adenine (A) is complementary to uracil (U). In certain embodiments, complementary nucleobase means a nucleobase of an antisense compound that is capable of base pairing with a nucleobase of its target nucleic acid. For example, if a nucleobase at a certain position of an antisense compound is capable of hydrogen bonding with a nucleobase at a certain position of a target nucleic acid, then the position of hydrogen bonding between the oligonucleotide and the target nucleic acid is considered to be complementary at that nucleobase pair. Nucleobases comprising certain modifications may maintain the ability to pair with a counterpart nucleobase and thus, are still capable of nucleobase complementarity.

As used herein, "non-complementary" in reference to nucleobases means a pair of nucleobases that do not form hydrogen bonds with one another.

As used herein, "complementary" in reference to oligomeric compounds (e.g., linked nucleosides, oligonucleotides, or nucleic acids) means the capacity of such oligomeric compounds or regions thereof to hybridize to another oligomeric compound or region thereof through nucleobase complementarity under stringent conditions. Complementary oligomeric compounds need not have nucleobase complementarity at each nucleoside. Rather, some mismatches are tolerated. In certain embodiments, complementary oligomeric compounds or regions are complementary at 70% of the nucleobases (70% complementary). In certain embodiments, complementary oligomeric compounds or regions are 80% complementary. In certain embodiments, complementary oligomeric compounds or regions are 90% complementary. In certain embodiments, complementary oligomeric compounds or regions are 95% complementary. In certain embodiments, complementary oligomeric compounds or regions are 100% complementary.

As used herein, "hybridization" means the pairing of complementary oligomeric compounds (e.g., an antisense compound and its target nucleic acid). While not limited to a particular mechanism, the most common mechanism of pairing involves hydrogen bonding, which may be Watson-Crick, Hoogsteen or reversed Hoogsteen hydrogen bonding, between complementary nucleobases.

As used herein, "specifically hybridizes" means the ability of an oligomeric compound to hybridize to one nucleic acid site with greater affinity than it hybridizes to another nucleic acid site. In certain embodiments, an antisense oligonucleotide specifically hybridizes to more than one target site.

As used herein, "percent complementarity" means the percentage of nucleobases of an oligomeric compound that are complementary to an equal-length portion of a target nucleic acid. Percent complementarity is calculated by dividing the number of nucleobases of the oligomeric compound that are complementary to nucleobases at corresponding positions in the target nucleic acid by the total length of the oligomeric compound.

As used herein, "percent identity" means the number of nucleobases in a first nucleic acid that are the same type (independent of chemical modification) as nucleobases at corresponding positions in a second nucleic acid, divided by the total number of nucleobases in the first nucleic acid.

As used herein, "type of modification" in reference to a nucleoside or a nucleoside of a "type" means the chemical modification of a nucleoside and includes modified and unmodified nucleosides. Accordingly, unless otherwise indicated, a "nucleoside having a modification of a first type" may be an unmodified nucleoside.

As used herein, "differently modified" mean chemical modifications or chemical substituents that are different from one another, including absence of modifications. Thus, for example, a MOE nucleoside and an unmodified DNA nucleoside are "differently modified," even though the DNA nucleoside is unmodified. Likewise, DNA and RNA are "differently modified," even though both are naturally-occurring unmodified nucleosides. Nucleosides that are the same but for comprising different nucleobases are not differently modified. For example, a nucleoside comprising a 2'-OMe modified sugar and an unmodified adenine nucleobase and a nucleoside comprising a 2'-OMe modified sugar and an unmodified thymine nucleobase are not differently modified.

As used herein, "the same type of modifications" refers to modifications that are the same as one another, including absence of modifications. Thus, for example, two unmodified DNA nucleoside have "the same type of modification," even though the DNA nucleoside is unmodified. Such nucleosides having the same type modification may comprise different nucleobases.

As used herein, "substituent" and "substituent group," means an atom or group that replaces the atom or group of a named parent compound. For example a substituent of a modified nucleoside is any atom or group that differs from the atom or group found in a naturally occurring nucleoside (e.g., a modified 2'-substituent is any atom or group at the 2'-position of a nucleoside other than H or OH). Substituent groups can be protected or unprotected. In certain embodiments, compounds of the present invention have substituents at one or at more than one position of the parent compound. Substituents may also be further substituted with other substituent groups and may be attached directly or via a linking group such as an alkyl or hydrocarbyl group to a parent compound.

Likewise, as used herein, "substituent" in reference to a chemical functional group means an atom or group of atoms differs from the atom or a group of atoms normally present in the named functional group. In certain embodiments, a substituent replaces a hydrogen atom of the functional group (e.g., in certain embodiments, the substituent of a substituted methyl group is an atom or group other than hydrogen which replaces one of the hydrogen atoms of an unsubstituted methyl group). Unless otherwise indicated, groups amenable for use as substituents include without limitation, halogen, hydroxyl, alkyl, alkenyl, alkynyl, acyl (—C(O)$R_{aa}$), carboxyl (—C(O)O—$R_{aa}$), aliphatic groups, alicyclic groups, alkoxy, substituted oxy (—O—$R_{aa}$), aryl, aralkyl, heterocyclic radical, heteroaryl, heteroarylalkyl, amino (—N($R_{bb}$)($R_{cc}$)), imino (=$NR_{bb}$), amido (—C(O)N($R_{bb}$)($R_{cc}$) or —N($R_{bb}$)C(O)$R_{aa}$), azido (—$N_3$), nitro (—$NO_2$), cyano (—CN), carbamido (—OC(O)N($R_{bb}$)($R_{cc}$) or —N($R_{bb}$)C(O)O$R_{aa}$), ureido (—N($R_{bb}$)C(O)N($R_{bb}$)($R_{cc}$)), thioureido (—N($R_{bb}$)C(S)N($R_{bb}$)—($R_{cc}$)), guanidinyl (—N($R_{bb}$)C(=$NR_{bb}$)N($R_{bb}$)($R_{cc}$)), amidinyl (—C(=$NR_{bb}$)N($R_{bb}$)($R_{cc}$) or —N($R_{bb}$)C(=$NR_{bb}$)($R_{aa}$)), thiol (—$SR_{bb}$), sulfinyl (—S(O)$R_{bb}$), sulfonyl (—S(O)$_2R_{bb}$) and sulfonamidyl (—S(O)$_2$N($R_{bb}$)($R_{cc}$) or —N($R_{bb}$)S—(O)$_2R_{bb}$). Wherein each $R_{aa}$, $R_{bb}$ and $R_{cc}$ is, independently, H, an optionally linked chemical functional group or a further substituent group with a preferred list including without limitation, alkyl, alkenyl, alkynyl, aliphatic, alkoxy, acyl, aryl, aralkyl, heteroaryl, alicyclic, heterocyclic and heteroarylalkyl. Selected substituents within the compounds described herein are present to a recursive degree.

As used herein, "alkyl," as used herein, means a saturated straight or branched hydrocarbon radical containing up to twenty four carbon atoms. Examples of alkyl groups include without limitation, methyl, ethyl, propyl, butyl, isopropyl, n-hexyl, octyl, decyl, dodecyl and the like. Alkyl groups typically include from 1 to about 24 carbon atoms, more typically from 1 to about 12 carbon atoms ($C_1$-$C_{12}$ alkyl) with from 1 to about 6 carbon atoms being more preferred.

As used herein, "alkenyl," means a straight or branched hydrocarbon chain radical containing up to twenty four carbon atoms and having at least one carbon-carbon double bond. Examples of alkenyl groups include without limitation, ethenyl, propenyl, butenyl, 1-methyl-2-buten-1-yl, dienes such as 1,3-butadiene and the like. Alkenyl groups typically include from 2 to about 24 carbon atoms, more typically from 2 to about 12 carbon atoms with from 2 to about 6 carbon atoms being more preferred. Alkenyl groups as used herein may optionally include one or more further substituent groups.

As used herein, "alkynyl," means a straight or branched hydrocarbon radical containing up to twenty four carbon atoms and having at least one carbon-carbon triple bond. Examples of alkynyl groups include, without limitation, ethynyl, 1-propynyl, 1-butynyl, and the like. Alkynyl groups typically include from 2 to about 24 carbon atoms, more typically from 2 to about 12 carbon atoms with from 2 to about 6 carbon atoms being more preferred. Alkynyl groups as used herein may optionally include one or more further substituent groups.

As used herein, "acyl," means a radical formed by removal of a hydroxyl group from an organic acid and has the general Formula —C(O)—X where X is typically aliphatic, alicyclic or aromatic. Examples include aliphatic carbonyls, aromatic carbonyls, aliphatic sulfonyls, aromatic sulfinyls, aliphatic sulfinyls, aromatic phosphates, aliphatic phosphates and the like. Acyl groups as used herein may optionally include further substituent groups.

As used herein, "alicyclic" means a cyclic ring system wherein the ring is aliphatic. The ring system can comprise one or more rings wherein at least one ring is aliphatic. Preferred alicyclics include rings having from about 5 to about 9 carbon atoms in the ring. Alicyclic as used herein may optionally include further substituent groups.

As used herein, "aliphatic" means a straight or branched hydrocarbon radical containing up to twenty four carbon atoms wherein the saturation between any two carbon atoms is a single, double or triple bond. An aliphatic group preferably contains from 1 to about 24 carbon atoms, more typically from 1 to about 12 carbon atoms with from 1 to about 6 carbon atoms being more preferred. The straight or branched chain of an aliphatic group may be interrupted with one or more heteroatoms that include nitrogen, oxygen, sulfur and phosphorus. Such aliphatic groups interrupted by heteroatoms include without limitation, polyalkoxys, such as polyalkylene glycols, polyamines, and polyimines Aliphatic groups as used herein may optionally include further substituent groups.

As used herein, "alkoxy" means a radical formed between an alkyl group and an oxygen atom wherein the oxygen atom is used to attach the alkoxy group to a parent molecule. Examples of alkoxy groups include without limitation, methoxy, ethoxy, propoxy, isopropoxy, n-butoxy, sec-butoxy, tert-butoxy, n-pentoxy, neopentoxy, n-hexoxy and the like. Alkoxy groups as used herein may optionally include further substituent groups.

As used herein, "aminoalkyl" means an amino substituted $C_1$-$C_{12}$ alkyl radical. The alkyl portion of the radical forms a covalent bond with a parent molecule. The amino group can be located at any position and the aminoalkyl group can be substituted with a further substituent group at the alkyl and/or amino portions.

As used herein, "aralkyl" and "arylalkyl" mean an aromatic group that is covalently linked to a $C_1$-$C_{12}$ alkyl radical. The alkyl radical portion of the resulting aralkyl (or arylalkyl) group forms a covalent bond with a parent molecule. Examples include without limitation, benzyl, phenethyl and the like. Aralkyl groups as used herein may optionally include further substituent groups attached to the alkyl, the aryl or both groups that form the radical group.

As used herein, "aryl" and mean a mono- or polycyclic carbocyclic ring system radicals having one or more aromatic rings. Examples of aryl groups include without limitation, phenyl, naphthyl, tetrahydronaphthyl, indanyl, idenyl and the like. Preferred aryl ring systems have from about 5 to about 20 carbon atoms in one or more rings. Aryl groups as used herein may optionally include further substituent groups.

As used herein, "halo" and "halogen," mean an atom selected from fluorine, chlorine, bromine and iodine.

As used herein, "heteroaryl," mean a radical comprising a mono- or poly-cyclic aromatic ring, ring system or fused ring system wherein at least one of the rings is aromatic and includes one or more heteroatoms. Heteroaryl is also meant to include fused ring systems including systems where one or more of the fused rings contain no heteroatoms. Heteroaryl groups typically include one ring atom selected from sulfur, nitrogen or oxygen. Examples of heteroaryl groups include without limitation, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl and the like. Heteroaryl radicals can be attached to a parent molecule directly or through a linking moiety such as an aliphatic group or hetero atom. Heteroaryl groups as used herein may optionally include further substituent groups.

Oligonucleotides

In certain embodiments, the present invention provides compounds and methods for detecting target oligonucleotides in a biological sample. In such embodiments, the target oligonucleotide is an aptomer. Certain aptomers are known in the art. In certain embodiments, the target oligonucleotide is an antisense oligonucleotide. In certain embodiments, target oligonucleotides optionally comprise one or more conjugate and/or terminal groups. In certain embodiments, target oligonucleotides consist of an oligonucleotide without a conjugate. In certain embodiments, target oligonucleotides comprise one or more chemical modifications. Such chemical modifications include modifications one or more nucleoside (including modifications to the sugar moiety and/or the nucleobase) and/or modifications to one or more internucleoside linkage.

In certain embodiments, the probes described herein are oligonucleotides. Such probe oligonucleotides may comprise one or more modification, including, but not limited to modified sugar, modified base, and/or modified internucleoside linkages. Accordingly, the following discussion regarding such modifications may refer to target oligonucleotides and/or probe oligonucleotides.

Certain Sugar Moieties

In certain embodiments, oligonucleotides comprise one or more modified nucleosides comprising a modified sugar moiety. Such oligonucleotides comprising one or more sugar-modified nucleosides may have desirable properties, such as enhanced nuclease stability or increased binding affinity with a target nucleic acid relative to oligonucleotides comprising only nucleosides comprising naturally occurring sugar moieties. In certain embodiments, modified sugar moieties are substituted sugar moieties. In certain embodiments, modified sugar moieties are bicyclic or tricyclic sugar moieties. In certain embodiments, modified sugar moieties are sugar surrogates. Such sugar surrogates may comprise one or more substitutions corresponding to those of substituted sugar moieties.

In certain embodiments, modified sugar moieties are substituted sugar moieties comprising one or more substituent, including but not limited to substituents at the 2' and/or 5' positions. Examples of sugar substituents suitable for the 2'-position, include, but are not limited to: 2'-F, 2'-OCH$_3$ ("OMe" or "O-methyl"), and 2'-O(CH$_2$)$_2$OCH$_3$ ("MOE"). In certain embodiments, sugar substituents at the 2' position is selected from allyl, amino, azido, thio, O-allyl, O—C$_1$-C$_{10}$ alkyl, O—C$_1$-C$_{10}$ substituted alkyl; O—C$_1$-C$_{10}$ alkoxy; O—C$_1$-C$_{10}$ substituted alkoxy, OCF$_3$, O(CH$_2$)$_2$SCH$_3$, O(CH$_2$)$_2$—O—N(Rm)(Rn), and O—CH$_2$—C(=O)—N(Rm)(Rn), where each Rm and Rn is, independently, H or substituted or unsubstituted C$_1$-C$_{10}$ alkyl. Examples of sugar substituents at the 5'-position, include, but are not limited to: 5'-methyl (R or S); 5'-vinyl, and 5'-methoxy. In certain embodiments, substituted sugars comprise more than one non-bridging sugar substituent, for example, 2'-F-5'-methyl sugar moieties (see, e.g., PCT International Application WO 2008/101157, for additional 5', 2'-bis substituted sugar moieties and nucleosides).

Nucleosides comprising 2'-substituted sugar moieties are referred to as 2'-substituted nucleosides. In certain embodiments, a 2'-substituted nucleoside comprises a 2'-substituent group selected from halo, allyl, amino, azido, O—C$_1$-C$_{10}$ alkoxy; O—C$_1$-C$_{10}$ substituted alkoxy, SH, CN, OCN, CF$_3$, OCF$_3$, O-alkyl, S-alkyl, N(R$_m$)-alkyl; O-alkenyl, S-alkenyl, or N(R$_m$)-alkenyl; O-alkynyl, S-alkynyl, N(R$_m$)-alkynyl; O-alkylenyl-O-alkyl, alkynyl, alkaryl, aralkyl, O-alkaryl, O-aralkyl, O(CH$_2$)$_2$SCH$_3$, O—(CH$_2$)$_2$—O—N(R$_m$)(R$_n$) or O—CH$_2$—C(=O)—N(R$_m$)(R$_n$), where each R$_m$ and R$_n$ is, independently, H, an amino protecting group or substituted or unsubstituted C$_1$-C$_{10}$ alkyl. These 2'-substituent groups can be further substituted with one or more substituent groups independently selected from hydroxyl, amino, alkoxy, carboxy, benzyl, phenyl, nitro (NO$_2$), thiol, thioalkoxy (S-alkyl), halogen, alkyl, aryl, alkenyl and alkynyl.

In certain embodiments, a 2'-substituted nucleoside comprises a 2'-substituent group selected from F, NH$_2$, N$_3$, OCF$_3$, O—CH$_3$, O(CH$_2$)$_3$NH$_2$, CH$_2$—CH=CH$_2$, O—CH$_2$—CH=CH$_2$, OCH$_2$CH$_2$OCH$_3$, O(CH$_2$)$_2$SCH$_3$, O—(CH$_2$)$_2$—O—N(R$_m$)(R$_n$), O(CH$_2$)$_2$O(CH$_2$)$_2$N(CH$_3$)$_2$, and N-substituted acetamide (O—CH$_2$—C(=O)—N(R$_m$)(R$_n$)) where each R$_m$ and R$_n$ is, independently, H, an amino protecting group or substituted or unsubstituted C$_1$-C$_{10}$ alkyl.

In certain embodiments, a 2'-substituted nucleoside comprises a sugar moiety comprising a 2'-substituent group selected from F, OCF$_3$, O—CH$_3$, OCH$_2$CH$_2$OCH$_3$, O(CH$_2$)$_2$SCH$_3$, O—(CH$_2$)$_2$—O—N(CH$_3$)$_2$, —O(CH$_2$)$_2$O(CH$_2$)$_2$N(CH$_3$)$_2$, and O—CH$_2$—C(=O)—N(H)CH$_3$.

In certain embodiments, a 2'-substituted nucleoside comprises a sugar moiety comprising a 2'-substituent group selected from F, O—CH$_3$, and OCH$_2$CH$_2$OCH$_3$.

Certain modified sugar moieties comprise a bridging sugar substituent that forms a second ring resulting in a bicyclic sugar moiety. In certain such embodiments, the bicyclic sugar moiety comprises a bridge between the 4' and the 2' furanose ring atoms. Examples of such 4' to 2' sugar substituents, include, but are not limited to: —[C(R$_a$)(R$_b$)]$_n$—, —[C(R$_a$)(R$_b$)]$_n$—O—, —C(R$_a$R$_b$)—N(R)—O— or, —C(R$_a$R$_b$)—O—N(R)—; 4'-CH$_2$-2', 4'-(CH$_2$)$_2$-2', 4'-(CH$_2$)$_3$-2', 4'-(CH$_2$)—O-2' (LNA); 4'-(CH$_2$)—S-2; 4'-(CH$_2$)$_2$—O-2' (ENA); 4'-CH(CH$_3$)—O-2' (cEt) and 4'-CH(CH$_2$OCH$_3$)—O-2', and analogs thereof (see, e.g., U.S. Pat. No. 7,399,845, issued on Jul. 15, 2008); 4'-C(CH$_3$)(CH$_3$)—O-2' and analogs thereof, (see, e.g., WO2009/006478, published Jan. 8, 2009); 4'-CH$_2$—N(OCH$_3$)-2' and analogs thereof (see, e.g., WO2008/150729, published Dec. 11, 2008); 4'-CH$_2$—O—N(CH$_3$)-2' (see, e.g., US2004/0171570, published Sep. 2, 2004); 4'-CH$_2$—O—N(R)-2', and 4'-CH$_2$—N(R)—O-2'-, wherein each R is, independently, H, a protecting group, or C$_1$-C$_{12}$ alkyl; 4'-CH$_2$—N(R)—O-2', wherein R is H, C$_1$-C$_{12}$ alkyl, or a protecting group (see, U.S. Pat. No. 7,427,672, issued on Sep. 23, 2008); 4'-CH$_2$—C(H)(CH$_3$)-2' (see, e.g., Chattopadhyaya, et al., *J. Org. Chem.*, 2009, 74, 118-134); and 4'-CH$_2$—C(=CH$_2$)-2' and analogs thereof (see, published PCT International Application WO 2008/154401, published on Dec. 8, 2008).

In certain embodiments, such 4' to 2' bridges independently comprise from 1 to 4 linked groups independently selected from —[C(R$_a$)(R$_b$)]$_n$—, —C(R$_a$)=C(R$_b$)—, —C(R$_a$)=N—, —C(=NR$_a$)—, —C(=O)—, —C(=S)—, —O—, —Si(R$_a$)$_2$—, —S(=O)$_x$—, and —N(R$_a$)—;

wherein:

x is 0, 1, or 2;

n is 1, 2, 3, or 4;

each R$_a$ and R$_b$ is, independently, H, a protecting group, hydroxyl, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_5$-C$_{20}$ aryl, substituted C$_5$-C$_{20}$ aryl, heterocycle radical, substituted heterocycle radical, heteroaryl, substituted heteroaryl, C$_5$-C$_7$ alicyclic radical, substituted C$_5$-C$_7$ alicyclic radical, halogen, OJ$_1$, NJ$_1$J$_2$, SJ$_1$, N$_3$, COOJ$_1$, acyl (C(=O)—H), substituted acyl, CN, sulfonyl (S(=O)$_2$-J$_1$), or sulfoxyl (S(=O)-J$_1$); and each J$_1$ and J$_2$ is, independently, H, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_5$-C$_{20}$ aryl, substituted C$_5$-C$_{20}$ aryl, acyl (C(=O)—H), substituted acyl, a heterocycle radical, a substituted heterocycle radical, C$_1$-C$_{12}$ aminoalkyl, substituted C$_1$-C$_{12}$ aminoalkyl, or a protecting group.

Nucleosides comprising bicyclic sugar moieties are referred to as bicyclic nucleosides or BNAs. Bicyclic nucleosides include, but are not limited to, (A) α-L-Methyleneoxy (4'-CH$_2$—O-2') BNA, (B) β-D-Methyleneoxy (4'-CH$_2$—O-2') BNA (also referred to as locked nucleic acid or LNA), (C) Ethyleneoxy (4'-(CH$_2$)$_2$—O-2') BNA, (D) Aminooxy (4'-CH$_2$—O—N(R)-2') BNA, (E) Oxyamino (4'-CH$_2$—N(R)—O-2') BNA, (F) Methyl(methyleneoxy) (4'-CH(CH$_3$)—O-2') BNA (also referred to as constrained ethyl or cEt), (G) methylene-thio (4'-CH$_2$—S-2') BNA, (H) methylene-amino (4'-CH2-N(R)-2') BNA, (I) methyl carbocyclic (4'-CH$_2$—CH(CH$_3$)-2') BNA, and (J) propylene carbocyclic (4'-(CH$_2$)$_3$-2') BNA as depicted below.

(A)
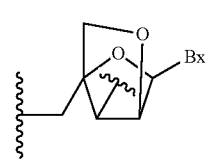

(B)
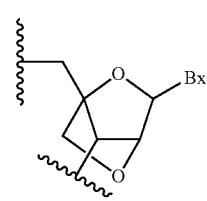

(C)
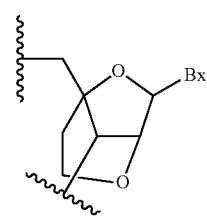

(D)
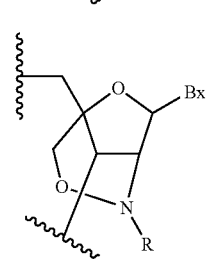

(E)
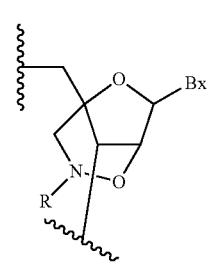

(F)
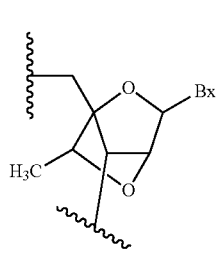

(G)
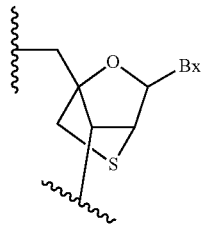

(H)
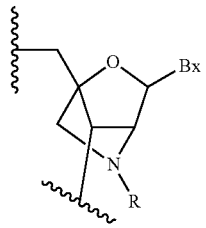

(I)
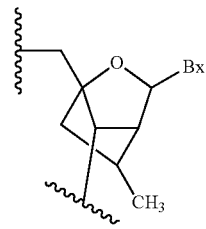

(J)

wherein Bx is a nucleobase moiety and R is, independently, H, a protecting group, or C$_1$-C$_{12}$ alkyl.

Additional bicyclic sugar moieties are known in the art, for example: Singh et al., *Chem. Commun.*, 1998, 4, 455-456; Koshkin et al., *Tetrahedron*, 1998, 54, 3607-3630; Wahlestedt et al., *Proc. Natl. Acad. Sci. U.S.A*, 2000, 97, 5633-5638; Kumar et al., *Bioorg. Med. Chem. Lett.*, 1998, 8, 2219-2222; Singh et al., *J. Org. Chem.*, 1998, 63, 10035-10039; Srivastava et al., *J. Am. Chem. Soc.*, 129(26) 8362-8379 (Jul. 4, 2007); Elayadi et al., *Curr. Opinion Invens. Drugs*, 2001, 2, 558-561; Braasch et al., *Chem. Biol.*, 2001, 8, 1-7; Orum et al., *Curr. Opinion Mol. Ther.*, 2001, 3, 239-243; U.S. Pat. Nos. 7,053,207, 6,268,490, 6,770,748, 6,794,499, 7,034,133, 6,525,191, 6,670,461, and 7,399,845; WO 2004/106356, WO 1994/14226, WO 2005/021570, and WO 2007/134181; U.S. Patent Publication Nos. US2004/0171570, US2007/0287831, and US2008/0039618; U.S. patent Ser. No. 12/129,154, 60/989,574, 61/026,995, 61/026,998, 61/056,564, 61/086,231, 61/097,787, and 61/099,844; and PCT International Applications Nos. PCT/US2008/064591, PCT/US2008/066154, and PCT/US2008/068922.

In certain embodiments, bicyclic sugar moieties and nucleosides incorporating such bicyclic sugar moieties are further defined by isomeric configuration. For example, a nucleoside comprising a 4'-2' methylene-oxy bridge, may be in the α-L configuration or in the β-D configuration. Previously, α-L-methyleneoxy (4'-CH$_2$—O-2') bicyclic nucleosides have been incorporated into antisense oligonucleotides that showed antisense activity (Frieden et al., *Nucleic Acids Research*, 2003, 21, 6365-6372).

In certain embodiments, substituted sugar moieties comprise one or more non-bridging sugar substituent and one or more bridging sugar substituent (e.g., 5'-substituted and 4'-2' bridged sugars). (see, PCT International Application WO 2007/134181, published on Nov. 22, 2007, wherein LNA is substituted with, for example, a 5'-methyl or a 5'-vinyl group).

In certain embodiments, modified sugar moieties are sugar surrogates. In certain such embodiments, the oxygen atom of the naturally occurring sugar is substituted, e.g., with a sulfer, carbon or nitrogen atom. In certain such embodiments, such modified sugar moiety also comprises bridging and/or non-bridging substituents as described above. For example, certain sugar surrogates comprise a 4'-sulfer atom and a substitution at the 2'-position (see, e.g., published U.S. Patent Application US2005/0130923, published on Jun. 16, 2005) and/or the 5' position. By way of additional example, carbocyclic bicyclic nucleosides having a 4'-2' bridge have been described (see, e.g., Freier et al., *Nucleic Acids Research*, 1997, 25(22), 4429-4443 and Albaek et al., *J. Org. Chem.*, 2006, 71, 7731-7740).

In certain embodiments, sugar surrogates comprise rings having other than 5-atoms. For example, in certain embodiments, a sugar surrogate comprises a six-membered tetrahydropyran. Such tetrahydropyrans may be further modified or substituted. Nucleosides comprising such modified tetrahydropyrans include, but are not limited to, hexitol nucleic acid (HNA), anitol nucleic acid (ANA), mannitol nucleic acid (MNA) (see Leumann, C J. *Bioorg. & Med. Chem.* (2002) 10:841-854), fluoro HNA (F-HNA), and those compounds having Formula VII:

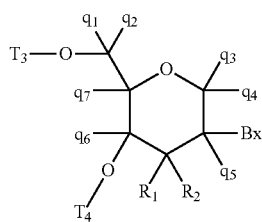

VII wherein independently for each of said at least one tetrahydropyran nucleoside analog of Formula VII:

Bx is a nucleobase moiety;

T$_3$ and T$_4$ are each, independently, an internucleoside linking group linking the tetrahydropyran nucleoside analog to the antisense compound or one of T$_3$ and T$_4$ is an internucleoside linking group linking the tetrahydropyran nucleoside analog to the antisense compound and the other of T$_3$ and T$_4$ is H, a hydroxyl protecting group, a linked conjugate group, or a 5' or 3'-terminal group;

q$_1$, q$_2$, q$_3$, q$_4$, q$_5$, q$_6$ and q$_7$ are each, independently, H, C$_1$-C$_6$ alkyl, substituted C$_1$-C$_6$ alkyl, C$_2$-C$_6$ alkenyl, substituted C$_2$-C$_6$ alkenyl, C$_2$-C$_6$ alkynyl, or substituted C$_2$-C$_6$ alkynyl; and each of R$_1$ and R$_2$ is independently selected from among: hydrogen, halogen, substituted or unsubstituted alkoxy, NJ$_1$J$_2$, SJ$_1$, N$_3$, OC(=X)J$_1$, OC(=X)NJ$_1$J$_2$, NJ$_3$C(=X) NJ$_1$J$_2$, and CN, wherein X is O, S or NJ$_1$, and each J$_1$, J$_2$, and J$_3$ is, independently, H or C$_1$-C$_6$ alkyl.

In certain embodiments, the modified THP nucleosides of Formula VII are provided wherein q$_1$, q$_2$, q$_3$, q$_4$, q$_5$, q$_6$ and q$_7$ are each H. In certain embodiments, at least one of q$_1$, q$_2$, q$_3$, q$_4$, q$_5$, q$_6$ and q$_7$ is other than H. In certain embodiments, at least one of q$_1$, q$_2$, q$_3$, q$_4$, q$_5$, q$_6$ and q$_7$ is methyl. In certain embodiments, THP nucleosides of Formula VII are provided wherein one of R$_1$ and R$_2$ is F. In certain embodiments, R$_1$ is fluoro and R$_2$ is H, R$_1$ is methoxy and R$_2$ is H, and R$_1$ is methoxyethoxy and R$_2$ is H.

Many other bicyclic and tricyclic sugar and sugar surrogate ring systems are known in the art that can be used to modify nucleosides (see, e.g., review article: Leumann, J. C, *Bioorganic & Medicinal Chemistry*, 2002, 10, 841-854).

In certain embodiments, sugar surrogates comprise rings having more than 5 atoms and more than one heteroatom. For example nucleosides comprising morpholino sugar moieties and their use in oligomeric compounds has been reported (see for example: Braasch et al., Biochemistry, 2002, 41, 4503-4510; and U.S. Pat. Nos. 5,698,685; 5,166, 315; 5,185,444; and 5,034,506). As used here, the term "morpholino" means a sugar surrogate having the following structure:

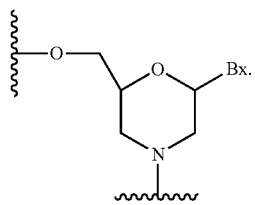

In certain embodiments, morpholinos may be modified, for example by adding or altering various substituent groups from the above morpholino structure. Such sugar surrogates are referred to herein as "modified morpholinos."

Combinations of modifications are also provided without limitation, such as 2'-F-5'-methyl substituted nucleosides (see PCT International Application WO 2008/101157 Published on Aug. 21, 2008 for other disclosed 5', 2'-bis substituted nucleosides) and replacement of the ribosyl ring oxygen atom with S and further substitution at the 2'-position (see published U.S. Patent Application US2005-0130923, published on Jun. 16, 2005) or alternatively 5'-substitution of a bicyclic nucleic acid (see PCT International Application WO 2007/134181, published on Nov. 22, 2007 wherein a 4'-CH$_2$—O-2' bicyclic nucleoside is further substituted at the 5' position with a 5'-methyl or a 5'-vinyl group). The synthesis and preparation of carbocyclic bicyclic nucleosides along with their oligomerization and biochemical studies have also been described (see, e.g., Srivastava et al., *J. Am. Chem. Soc.* 2007, 129(26), 8362-8379).

Certain Nucleobases

In certain embodiments, nucleosides of the present invention comprise one or more unmodified nucleobases. In certain embodiments, nucleosides of the present invention comprise one or more modified nucleobases.

In certain embodiments, modified nucleobases are selected from: universal bases, hydrophobic bases, promiscuous bases, size-expanded bases, and fluorinated bases as defined herein. 5-substituted pyrimidines, 6-azapyrimidines and N-2, N-6 and O-6 substituted purines, including 2-aminopropyladenine, 5-propynyluracil; 5-propynylcytosine; 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—CH$_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine, 3-deazaguanine and 3-deazaadenine, universal bases, hydrophobic bases, promiscuous bases, size-expanded bases, and fluorinated bases as defined herein. Further modified nucleobases include tricyclic pyrimidines such as phenoxazine cytidine([5,4-b][1,4]benzoxazin-2(3H)-one), phenothiazine cytidine (1H-pyrimido[5,4-b][1,4]benzothiazin-2(3H)-one), G-clamps such as a substituted phenoxazine cytidine (e.g. 9-(2-aminoethoxy)-H-pyrimido[5,4-b][1,4]benzoxazin-2(3H)-one), carbazole cytidine (2H-pyrimido[4,5-b]indol-2-one), pyridoindole cytidine (H-pyrido[3',2':4,5]pyrrolo[2,3-d]pyrimidin-2-one). Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in *The Concise Encyclopedia Of Polymer Science And Engineering*, Kroschwitz, J. I., Ed., John Wiley & Sons, 1990, 858-859; those disclosed by Englisch et al., *Angewandte Chemie*, International Edition, 1991, 30, 613; and those disclosed by Sanghvi, Y. S., Chapter 15, *Antisense Research and Applications*, Crooke, S. T. and Lebleu, B., Eds., CRC Press, 1993, 273-288.

Representative United States patents that teach the preparation of certain of the above noted modified nucleobases as well as other modified nucleobases include without limitation, U.S. Pat. Nos. 3,687,808; 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; 5,645,985; 5,681,941; 5,750,692; 5,763,588; 5,830,653 and 6,005,096, certain of which are commonly owned with the instant application, and each of which is herein incorporated by reference in its entirety.

Certain Internucleoside Linkages

In certain embodiments, the present invention provides oligomeric compounds comprising linked nucleosides. In such embodiments, nucleosides may be linked together using any internucleoside linkage. The two main classes of internucleoside linking groups are defined by the presence or absence of a phosphorus atom. Representative phosphorus containing internucleoside linkages include, but are not limited to, phosphodiesters (P=O), phosphotriesters, methylphosphonates, phosphoramidate, and phosphorothioates (P=S). Representative non-phosphorus containing internucleoside linking groups include, but are not limited to, methylenemethylimino (—CH$_2$—N(CH$_3$)—O—CH$_2$—), thiodiester (—O—C(O)—S—), thionocarbamate (—O—C(O)(NH)—S—); siloxane (—O—Si(H)$_2$—O—); and N,N'-dimethylhydrazine (—CH$_2$—N(CH$_3$)—N(CH$_3$)—). Modified linkages, compared to natural phosphodiester linkages, can be used to alter, typically increase, nuclease resistance of the oligomeric compound. In certain embodiments, internucleoside linkages having a chiral atom can be prepared as a racemic mixture, or as separate enantiomers. Representative chiral linkages include, but are not limited to, alkylphosphonates and phosphorothioates. Methods of preparation of phosphorous-containing and non-phosphorous-containing internucleoside linkages are well known to those skilled in the art.

The oligonucleotides described herein contain one or more asymmetric centers and thus give rise to enantiomers, diastereomers, and other stereoisomeric configurations that may be defined, in terms of absolute stereochemistry, as (R) or (S), α or β such as for sugar anomers, or as (D) or (L) such as for amino acids etc. Included in the antisense compounds provided herein are all such possible isomers, as well as their racemic and optically pure forms.

Neutral internucleoside linkages include without limitation, phosphotriesters, methylphosphonates, MMI (3'-CH$_2$—N(CH$_3$)—O-5'), amide-3 (3'-CH$_2$—C(=O)—N(H)-5'), amide-4 (3'-CH$_2$—N(H)—C(=O)-5'), formacetal (3'-O—CH$_2$—O-5'), and thioformacetal (3'-S—CH$_2$—O-5'). Further neutral internucleoside linkages include nonionic linkages comprising siloxane (dialkylsiloxane), carboxylate ester, carboxamide, sulfide, sulfonate ester and amides (See for example: *Carbohydrate Modifications in Antisense Research*; Y. S. Sanghvi and P. D. Cook, Eds., ACS Symposium Series 580; Chapters 3 and 4, 40-65). Further neutral internucleoside linkages include nonionic linkages comprising mixed N, O, S and CH$_2$ component parts.

Certain Motifs

In certain embodiments, such oligonucleotides comprise one or more chemical modification. In certain embodiments, chemically modified oligonucleotides comprise one or more modified nucleosides. In certain embodiments, chemically modified oligonucleotides comprise one or more modified nucleosides comprising modified sugars. In certain embodiments, chemically modified oligonucleotides comprise one or more modified nucleosides comprising one or more modified nucleobases. In certain embodiments, chemically modified oligonucleotides comprise one or more modified internucleoside linkages. In certain embodiments, the chemically modifications (sugar modifications, nucleobase modifications, and/or linkage modifications) define a pattern or motif. In certain embodiments, the patterns of chemical modifications of sugar moieties, internucleoside linkages, and nucleobases are each independent of one another. Thus, an oligonucleotide may be described by its sugar modification motif, internucleoside linkage motif and/or nucleobase modification motif (as used herein, nucleobase modification motif describes the chemical modifications to the nucleobases independent of the sequence of nucleobases).

Certain Sugar Motifs

In certain embodiments, oligonucleotides comprise one or more type of modified sugar moieties and/or naturally occurring sugar moieties arranged along an oligonucleotide or region thereof in a defined pattern or sugar modification motif Such motifs may include any of the sugar modifications discussed herein and/or other known sugar modifications.

In certain embodiments, the oligonucleotides comprise or consist of a region having a gapmer sugar modification motif, which comprises two external regions or "wings" and an internal region or "gap." The three regions of a gapmer motif (the 5'-wing, the gap, and the 3'-wing) form a contiguous sequence of nucleosides wherein at least some of the sugar moieties of the nucleosides of each of the wings differ from at least some of the sugar moieties of the nucleosides of the gap. Specifically, at least the sugar moieties of the nucleosides of each wing that are closest to the gap (the 3'-most nucleoside of the 5'-wing and the 5'-most nucleoside of the 3'-wing) differ from the sugar moiety of the neighboring gap nucleosides, thus defining the boundary between the wings and the gap. In certain embodiments, the sugar moieties within the gap are the same as one another. In certain embodiments, the gap includes one or more nucleoside having a sugar moiety that differs from the sugar moiety of one or more other nucleosides of the gap. In certain embodiments, the sugar modification motifs of the two wings are the same as one another (symmetric gapmer). In certain embodiments, the sugar modification motifs of the 5'-wing differs from the sugar modification motif of the 3'-wing (asymmetric gapmer). In certain embodiments, oligonucleotides comprise 2'-MOE modified nucleosides in the wings and 2'-F modified nucleosides in the gap.

In certain embodiments, oligonucleotides are fully modified. In certain such embodiments, oligonucleotides are uniformly modified. In certain embodiments, oligonucleotides are uniform 2'-MOE. In certain embodiments, oligonucleotides are uniform 2'-F. In certain embodiments, oligonucleotides are uniform morpholino. In certain embodiments, oligonucleotides are uniform BNA. In certain embodiments, oligonucleotides are uniform LNA. In certain embodiments, oligonucleotides are uniform cEt.

In certain embodiments, oligonucleotides comprise a uniformly modified region and additional nucleosides that are unmodified or differently modified. In certain embodiments, the uniformly modified region is at least 5, 10, 15, or 20 nucleosides in length. In certain embodiments, the uniform region is a 2'-MOE region. In certain embodiments, the uniform region is a 2'-F region. In certain embodiments, the uniform region is a morpholino region. In certain embodiments, the uniform region is a BNA region. In certain embodiments, the uniform region is a LNA region. In certain embodiments, the uniform region is a cEt region.

In certain embodiments, the oligonucleotide does not comprise more than 4 contiguous unmodified 2'-deoxynucleosides. In certain circumstances, antisense oligonucleotides comprising more than 4 contiguous 2'-deoxynucleosides activate RNase H, resulting in cleavage of the target RNA. In certain embodiments, such cleavage is avoided by not having more than 4 contiguous 2'-deoxynucleosides, for example, where alteration of splicing and not cleavage of a target RNA is desired.

Certain Internucleoside Linkage Motifs

In certain embodiments, oligonucleotides comprise modified internucleoside linkages arranged along the oligonucleotide or region thereof in a defined pattern or modified internucleoside linkage motif. In certain embodiments, internucleoside linkages are arranged in a gapped motif, as described above for sugar modification motif. In such embodiments, the internucleoside linkages in each of two wing regions are different from the internucleoside linkages in the gap region. In certain embodiments the internucleoside linkages in the wings are phosphodiester and the internucleoside linkages in the gap are phosphorothioate. The sugar modification motif is independently selected, so such oligonucleotides having a gapped internucleoside linkage motif may or may not have a gapped sugar modification motif and if it does have a gapped sugar motif, the wing and gap lengths may or may not be the same.

In certain embodiments, oligonucleotides comprise a region having an alternating internucleoside linkage motif. In certain embodiments, oligonucleotides of the present invention comprise a region of uniformly modified internucleoside linkages. In certain such embodiments, the oligonucleotide comprises a region that is uniformly linked by phosphorothioate internucleoside linkages. In certain embodiments, the oligonucleotide is uniformly linked by phosphorothioate. In certain embodiments, each internucleoside linkage of the oligonucleotide is selected from phosphodiester and phosphorothioate. In certain embodiments, each internucleoside linkage of the oligonucleotide is selected from phosphodiester and phosphorothioate and at least one internucleoside linkage is phosphorothioate.

In certain embodiments, the oligonucleotide comprises at least 6 phosphorothioate internucleoside linkages. In certain embodiments, the oligonucleotide comprises at least 8 phosphorothioate internucleoside linkages. In certain embodiments, the oligonucleotide comprises at least 10 phosphorothioate internucleoside linkages. In certain embodiments, the oligonucleotide comprises at least one block of at least 6 consecutive phosphorothioate internucleoside linkages. In certain embodiments, the oligonucleotide comprises at least one block of at least 8 consecutive phosphorothioate internucleoside linkages. In certain embodiments, the oligonucleotide comprises at least one block of at least 10 consecutive phosphorothioate internucleoside linkages. In certain embodiments, the oligonucleotide comprises at least block of at least one 12 consecutive phosphorothioate internucleoside linkages. In certain such embodiments, at least one such block is located at the 3' end of the oligonucleotide. In certain such embodiments, at least one such block is located within 3 nucleosides of the 3' end of the oligonucleotide.

Certain Nucleobase Modification Motifs

In certain embodiments, oligonucleotides comprise chemical modifications to nucleobases arranged along the oligonucleotide or region thereof in a defined pattern or nucleobases modification motif. In certain such embodiments, nucleobase modifications are arranged in a gapped motif. In certain embodiments, nucleobase modifications are arranged in an alternating motif. In certain embodiments, each nucleobase is modified. In certain embodiments, none of the nucleobases is chemically modified.

In certain embodiments, oligonucleotides comprise a block of modified nucleobases. In certain such embodiments, the block is at the 3'-end of the oligonucleotide. In certain embodiments the block is within 3 nucleotides of the 3'-end of the oligonucleotide. In certain such embodiments, the block is at the 5'-end of the oligonucleotide. In certain embodiments the block is within 3 nucleotides of the 5'-end of the oligonucleotide.

In certain embodiments, nucleobase modifications are a function of the natural base at a particular position of an oligonucleotide. For example, in certain embodiments each purine or each pyrimidine in an oligonucleotide is modified. In certain embodiments, each adenine is modified. In certain embodiments, each guanine is modified. In certain embodiments, each thymine is modified. In certain embodiments, each cytosine is modified. In certain embodiments, each uracil is modified.

In certain embodiments, some, all, or none of the cytosine moieties in an oligonucleotide are 5-methyl cytosine moieties. Herein, 5-methyl cytosine is not a "modified nucleobase." Accordingly, unless otherwise indicated, unmodified nucleobases include both cytosine residues having a 5-methyl and those lacking a 5 methyl. In certain embodiments, the methylation state of all or some cytosine nucleobases is specified.

Certain Overall Lengths

In certain embodiments, the present invention provides oligomeric compounds including oligonucleotides of any of a variety of ranges of lengths. In certain embodiments, the invention provides oligomeric compounds or oligonucleotides consisting of X to Y linked nucleosides, where X represents the fewest number of nucleosides in the range and Y represents the largest number of nucleosides in the range. In certain such embodiments, X and Y are each independently selected from 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50; provided that X≤Y.

Certain Oligonucleotides

In certain embodiments, oligonucleotides of the present invention are characterized by their sugar motif, internucleoside linkage motif, nucleobase modification motif and overall length. In certain embodiments, such parameters are each independent of one another. Thus, each internucleoside linkage of an oligonucleotide having a gapmer sugar motif may be modified or unmodified and may or may not follow the gapmer modification pattern of the sugar modifications. Thus, the internucleoside linkages within the wing regions of a sugar-gapmer may be the same or different from one another and may be the same or different from the internucleoside linkages of the gap region. Likewise, such sugar-gapmer oligonucleotides may comprise one or more modified nucleobase independent of the gapmer pattern of the sugar modifications. Herein if a description of an oligonucleotide or oligomeric compound is silent with respect to one or more parameter, such parameter is not limited. Thus, an oligomeric compound described only as having a gapmer sugar motif without further description may have any length, internucleoside linkage motif, and nucleobase modification motif Unless otherwise indicated, all chemical modifications are independent of nucleobase sequence.

Certain Conjugate Groups

In certain embodiments, oligomeric compounds are modified by attachment of one or more conjugate groups. In general, conjugate groups modify one or more properties of the attached oligomeric compound including but not limited to pharmacodynamics, pharmacokinetics, stability, binding, absorption, cellular distribution, cellular uptake, charge and clearance. Conjugate groups are routinely used in the chemical arts and are linked directly or via an optional conjugate linking moiety or conjugate linking group to a parent compound such as an oligomeric compound, such as an oligonucleotide. Conjugate groups includes without limitation, intercalators, reporter molecules, polyamines, polyamides, polyethylene glycols, thioethers, polyethers, cholesterols, thiocholesterols, cholic acid moieties, folate, lipids, phospholipids, biotin, phenazine, phenanthridine, anthraquinone, adamantane, acridine, fluoresceins, rhodamines, coumarins and dyes. Certain conjugate groups have been described previously, for example: cholesterol moiety (Letsinger et al., Proc. Natl. Acad. Sci. USA, 1989, 86, 6553-6556), cholic acid (Manoharan et al., Bioorg. Med. Chem. Let., 1994, 4, 1053-1060), a thioether, e.g., hexyl-S-tritylthiol (Manoharan et al., Ann. N.Y. Acad. Sci., 1992, 660, 306-309; Manoharan et al., Bioorg. Med. Chem. Let., 1993, 3, 2765-2770), a thiocholesterol (Oberhauser et al., Nucl. Acids Res., 1992, 20, 533-538), an aliphatic chain, e.g., do-decan-diol or undecyl residues (Saison-Behmoaras et al., EMBO J., 1991, 10, 1111-1118; Kabanov et al., FEBS Lett., 1990, 259, 327-330; Svinarchuk et al., Biochimie, 1993, 75, 49-54), a phospholipid, e.g., di-hexadecyl-rac-glycerol or triethyl-ammonium 1,2-di-O-hexadecyl-rac-glycero-3-H-phosphonate (Manoharan et al., Tetrahedron Lett., 1995, 36, 3651-3654; Shea et al., Nucl. Acids Res., 1990, 18, 3777-3783), a polyamine or a polyethylene glycol chain (Manoharan et al., Nucleosides & Nucleotides, 1995, 14, 969-973), or adamantane acetic acid (Manoharan et al., Tetrahedron Lett., 1995, 36, 3651-3654) a palmityl moiety (Mishra et al., Biochim. Biophys. Acta, 1995, 1264, 229-237), or an octadecylamine or hexylamino-carbonyl-oxycholesterol moiety (Crooke et al., J. Pharmacol. Exp. Ther., 1996, 277, 923-937).

In certain embodiments, a conjugate group comprises an active drug substance, for example, aspirin, warfarin, phenylbutazone, ibuprofen, suprofen, fen-bufen, ketoprofen, (S)-(+)-pranoprofen, carprofen, dansylsarcosine, 2,3,5-triiodobenzoic acid, flufenamic acid, folinic acid, a benzothiadiazide, chlorothiazide, a diazepine, indo-methicin, a barbiturate, a cephalosporin, a sulfa drug, an antidiabetic, an antibacterial or an antibiotic.

In certain embodiments, conjugate groups are directly attached to oligonucleotides in oligomeric compounds. In certain embodiments, conjugate groups are attached to oligonucleotides by a conjugate linking group. In certain such embodiments, conjugate linking groups, including, but not limited to, bifunctional linking moieties such as those known in the art are amenable to the compounds provided herein. Conjugate linking groups are useful for attachment of conjugate groups, such as chemical stabilizing groups, functional groups, reporter groups and other groups to selective sites in a parent compound such as for example an oligomeric compound. In general a bifunctional linking moiety comprises a hydrocarbyl moiety having two functional groups. One of the functional groups is selected to bind to a parent molecule or compound of interest and the other is selected to bind essentially any selected group such as chemical functional group or a conjugate group. In some embodiments, the conjugate linker comprises a chain structure or an oligomer of repeating units such as ethylene glycol or amino acid units. Examples of functional groups that are routinely used in a bifunctional linking moiety include, but are not limited to, electrophiles for reacting with nucleophilic groups and nucleophiles for reacting with electrophilic groups. In some embodiments, bifunctional linking moieties include amino, hydroxyl, carboxylic acid, thiol, unsaturations (e.g., double or triple bonds), and the like.

Some nonlimiting examples of conjugate linking moieties include pyrrolidine, 8-amino-3,6-dioxaoctanoic acid (ADO), succinimidyl 4-(N-maleimidomethyl) cyclohexane-1-carboxylate (SMCC) and 6-aminohexanoic acid (AHEX or AHA). Other linking groups include, but are not limited to, substituted $C_1$-$C_{10}$ alkyl, substituted or unsubstituted $C_2$-$C_{10}$ alkenyl or substituted or unsubstituted $C_2$-$C_{10}$ alkynyl, wherein a nonlimiting list of preferred substituent groups includes hydroxyl, amino, alkoxy, carboxy, benzyl, phenyl, nitro, thiol, thioalkoxy, halogen, alkyl, aryl, alkenyl and alkynyl.

Conjugate groups may be attached to either or both ends of an oligonucleotide (terminal conjugate groups) and/or at any internal position.

In certain embodiments, conjugate groups are at the 3'-end of an oligonucleotide of an oligomeric compound. In certain embodiments, conjugate groups are near the 3'-end. In certain embodiments, conjugates are attached at the 3' end of an oligomeric compound, but before one or more terminal group nucleosides. In certain embodiments, conjugate groups are placed within a terminal group. In certain embodiments, the present invention provides oligomeric compounds. In certain embodiments, oligomeric compounds comprise an oligonucleotide. In certain embodiments, an oligomeric compound comprises an oligonucleotide and one or more conjugate and/or terminal groups. Such conjugate and/or terminal groups may be added to oligonucleotides having any of the chemical motifs discussed above. Thus, for example, an oligomeric compound comprising an oligonucleotide having region of alternating nucleosides may comprise a terminal group.

Antisense Oligonucleotides

In certain embodiments, oligonucleotides used in the present invention are antisense oligonucleotides. Such antisense oligonucleotides are capable of hybridizing to a target nucleic acid, resulting in at least one antisense activity. In certain embodiments, antisense oligonucleotides specifically hybridize to one or more target nucleic acid. In certain embodiments, a specifically hybridizing antisense oligonucleotides has a nucleobase sequence comprising a region having sufficient complementarity to a target nucleic acid to allow hybridization and result in antisense activity and insufficient complementarity to any non-target so as to avoid non-specific hybridization to any non-target nucleic acid sequences under conditions in which specific hybridization is desired (e.g., under physiological conditions for in vivo or therapeutic uses, and under conditions in which assays are performed in the case of in vitro assays).

In certain embodiments, the present invention provides antisense oligonucleotides that are fully complementary to the target nucleic acid over the entire length of the oligonucleotide. In certain embodiments, oligonucleotides are 99% complementary to the target nucleic acid. In certain embodiments, oligonucleotides are 95% complementary to the target nucleic acid. In certain embodiments, such oligonucleotides are 90% complementary to the target nucleic acid.

Antisense oligonucleotides exert activity through mechanisms involving the hybridization with one or more target nucleic acid, wherein the hybridization results in a biological effect. In certain embodiments, such hybridization results in target nucleic acid degradation and/or occupancy with concomitant inhibition or stimulation of the cellular machinery involving, for example, translation, transcription, splicing or polyadenylation of the target nucleic acid or of a nucleic acid with which the target nucleic acid may otherwise interact.

In certain embodiments, antisense activity results at least in part from degradation of target RNA by RNase H. RNase H is a cellular endonuclease which cleaves the RNA strand of an RNA:DNA duplex. It is known in the art that single-stranded antisense compounds which are DNA or "DNA-like" hybridize to RNA to elicit RNase H mediated activity in mammalian cells. Activation of RNase H, therefore, results in cleavage of the RNA target, thereby greatly enhancing the efficiency of DNA-like oligonucleotide-mediated inhibition of gene expression.

Antisense mechanisms also include, without limitation RNAi mechanisms, which utilize the RISC pathway. Such RNAi mechanisms include, without limitation siRNA, ssRNA and microRNA mechanisms. Such mechanisms include creation of a microRNA mimic and/or an anti-microRNA. To be suitable for RNAi, antisense compounds may be single- or double-stranded and include one or more RNA or RNA-like nucleosides.

In certain embodiments, the target nucleic acid is a pre-mRNA. In certain embodiments, an antisense oligonucleotide modulates splicing of a pre-mRNA. In certain embodiments, antisense compounds alter splicing by hybridizing to a pre-mRNA and disrupting an interaction that is necessary for normal splicing. In certain embodiments, antisense compounds alter splicing by hybridizing to a pre-mRNA and recruiting one or more proteins that elicit splicing.

Antisense mechanisms also include, without limitation, mechanisms that hybridize or mimic non-coding RNA other than microRNA or mRNA. Such non-coding RNA includes, but is not limited to promoter-directed RNA and short and long RNA that effects transcription or translation of one or more nucleic acids.

In certain embodiments, antisense oligonucleotides specifically hybridize when there is a sufficient degree of complementarity to avoid non-specific binding of the antisense compound to non-target nucleic acid sequences under conditions in which specific binding is desired, i.e., under physiological conditions in the case of in vivo assays or therapeutic treatment, and under conditions in which assays are performed in the case of in vitro assays.

It is understood in the art that incorporation of nucleotide affinity modifications may allow for a greater number of mismatches compared to an unmodified compound. Similarly, certain oligonucleotide sequences may be more tolerant to mismatches than other oligonucleotide sequences. One of ordinary skill in the art is capable of determining an appropriate number of mismatches between oligonucleotides, or between an oligonucleotide and a target nucleic acid, such as by determining melting temperature ($T_m$). $T_m$ or $\Delta T_m$ can be calculated by techniques that are familiar to one of ordinary skill in the art. For example, techniques described in Freier et al. (*Nucleic Acids Research,* 1997, 25, 22: 4429-4443) allow one of ordinary skill in the art to evaluate nucleotide modifications for their ability to increase the melting temperature of an RNA:DNA duplex.

In certain embodiments, oligonucleotides for use in the present invention are RNAi compounds. In certain embodiments, oligonucleotides for use in the present invention are ssRNA compounds. In certain embodiments, oligonucleotides for use in the present invention are paired with a second oligomeric compound to form an siRNA. In certain embodiments, the oligonucleotide for use in the present invention is the sense strand in an siRNA compound. In certain embodiments, the oligonucleotide for use in the present invention is the antisense strand in an siRNA compound.

Certain Assays

In certain embodiments, the present invention provides assays for determining the presence or amount of a target oligonucleotide, such as oligonucleotides having any of the modifications described herein, in a biological sample. For example, an antisense oligonucleotide or aptomer may be administered to an animal, including but not limited to a human. It may be desired to determine the presence or amount of that administered oligonucleotide in one or more biological fluid or tissue some time after administration.

In certain embodiments, the present invention employs hybridization probes. In certain such embodiments, a capture probe is complementary to a first portion of the oligonucleotide and a detector probe is complementary to a second portion of the oligonucleotide. The first and second portions do not overlap, thus allowing both probes to be simultaneously hybridized to the oligonucleotide. It is noted that in certain embodiments, the probes are oligonucleotides having a binding moiety or a detectable tag. In certain embodiments, the detectable tag is an electrochemiluminescent tag. As such, probes may comprise any modification amenable to oligonucleotides discussed herein. Accordingly in certain embodiments, probe oligonucleotides comprise one or more sugar, base or linkage modification.

Capture Probes

In certain embodiments the capture probe comprises a binding moiety conjugated to the 3'- or 5'-end of the probe.

In certain embodiments the binding moiety is biotin. In certain embodiments, the capture probe comprises one or more 5'-methyl cytosine in place of unmodified cytosine. In certain embodiments, all nucleosides of the capture probe contain 2'-sugar modifications. In certain embodiments, the capture probe contains two different 2'-sugar modifications selected from 2'-MOE and cEt; or 2'-fluoro and cEt. In certain embodiments, a capture probe comprises one modified nucleoside. In certain embodiments, a capture probe comprises two modified nucleosides. In certain embodiments, a capture probe comprises three modified nucleosides. In certain embodiments, a capture probe comprises four modified nucleosides. In certain embodiments, a capture probe comprises five modified nucleosides. In certain embodiments, a capture probe comprises at least six modified nucleosides. In certain embodiments in which a capture probe comprises more than one modified nucleoside, the modifications are all the same as one another. In certain embodiments comprising more than one modified nucleoside, at least two modifications are different from one another.

Detector Probes

In certain embodiments the detector probe comprises a detectable tag conjugated to the 3'- or 5'-end of the probe. In certain embodiments the detectable tag is an ECL tag. In certain embodiments, the detector probe comprises one or more 5'-methyl cytosine in place of unmodified cytosine. In certain embodiments, all nucleosides of the detector probe contain 2'-sugar modifications. In certain embodiments, the fully 2'-modified detector probe contains two different 2'-sugar modifications selected from 2'-MOE and cEt; or 2'-fluoro and cEt. In certain embodiments, the fully 2'-modified detector probe contains three different 2'-sugar modifications. In other certain embodiments, the detector probe is not fully 2'-modified, in which case 1-5 sugars are unmodified (2'-deoxy). In certain embodiments, a detector probe comprises three modified nucleosides. In certain embodiments, a detector probe comprises four modified nucleosides. In certain embodiments, a detector probe comprises five modified nucleosides. In certain embodiments, a detector probe comprises at least six modified nucleosides. In certain embodiments in which a detector probe comprises more than one modified nucleoside, the modifications are all the same as one another. In certain embodiments comprising more than one modified nucleoside, at least two modifications are different from one another.

Assay Method

The oligonucleotide detection method of the present invention, referred to herein as the "dual probe ECL method", is summarized in FIG. 1. A target oligonucleotide, in certain embodiments, a target oligonucleotide which has been administered to a subject, is detected by obtaining a sample of bodily fluid and/or extract from the subject and contacting the sample with a capture probe that has a sequence that is complementary to a first portion of the target oligonucleotide and with a detector probe that has a sequence that is complementary to a second portion of the target oligonucleotide. The first and second portions of the target oligonucleotide do not overlap such that the capture and detector probes may simultaneously hybridize to the target oligonucleotide. The capture probe of the present invention comprises a binding moiety that is covalently bound to the probe and which allows binding of the probe to a solid support to which the binding partner of the binding moiety is already bound. Solid supports include, for example, beads, culture dishes and 96-well plates. In a preferred embodiment, the binding moiety is biotin, which binds to a streptavidin-coated solid support. The detector probe of the present invention comprises a detectable moiety that is covalently bound to the probe and which allows detection of the target oligonucleotide—probe complex. In certain embodiments, the detectable marker is an ECL tag, which is incorporated into the probe using a NHS-ester derivative of the ECL tag conjugated to an amino-modified oligonucleotide probe. Both the bound (detector probe+ target oligonucleotide) and unbound detector probes are present following the contact of the detector probe with the target oligonucleotide. In order to remove unbound detector probe, the solid support is washed prior to detection to remove molecules that are not bound to the solid support either directly or indirectly via oligonucleotide hybridization. Detection and quantitation are accomplished via the detectable moiety. For example, an ECL tag can be excited and the emitted light measured by an imaging instrument. One of skill will appreciate that certain steps of the above method may be done in different order as described.

Target oligonucleotides that are administered to a subject may be bound by antibodies generated by the subject. Such antibodies may interfere with oligonucleotide detection by reducing binding of the probes to the oligonucleotide analyte. In order to prevent antibodies from interfering with oligonucleotide detection, certain embodiments of the present invention comprise addition of a protease to the test sample to digest the antibody. In certain embodiments, the protease is Proteinase K. In certain embodiments, the protease is added to the test sample at the same time as the capture probe.

Although tris(2,2-bipyridine) Ruthenium (II) is exemplified herein as the detectable marker, the use of any detectable marker capable of being incorporated into an oligonucleotide probe is within the scope of the present invention. Various detectable markers have been discussed in the art and each marker has a well known protocol for its use and detection. Such protocols or approaches can include, but are not limited to, fluorometric measurement, autoradiographic measurement, colorimetric measurement, visual observation, chemiluminescent measurement, electrochemical measurement and the like. Similarly, although the biotin-streptavindin system is used in the examples described herein, any suitable binding pair may be used to bind the probe to the solid support, including antibody-coated solid supports and antigen-conjugated probes.

Nonlimiting Disclosure and Incorporation by Reference

While certain compounds, compositions and methods described herein have been described with specificity in accordance with certain embodiments, the following examples serve only to illustrate the compounds described herein and are not intended to limit the same. Each of the references, GenBank accession numbers, and the like recited in the present application is incorporated herein by reference in its entirety.

Although the sequence listing accompanying this filing identifies each sequence as either "RNA" or "DNA" as required, in reality, those sequences may be modified with any combination of chemical modifications. One of skill in the art will readily appreciate that such designation as "RNA" or "DNA" to describe modified oligonucleotides is, in certain instances, arbitrary. For example, an oligonucleotide comprising a nucleoside comprising a 2'-OH sugar moiety and a thymine base could be described as a DNA having a modified sugar (2'-OH for the natural 2'-H of DNA) or as an RNA having a modified base (thymine (methylated uracil) for natural uracil of RNA).

Accordingly, nucleic acid sequences provided herein, including, but not limited to those in the sequence listing, are intended to encompass nucleic acids containing any combination of natural or modified RNA and/or DNA, including, but not limited to such nucleic acids having modified nucleobases. By way of further example and without limitation, an oligomeric compound having the nucleobase sequence "ATCGATCG" encompasses any oligomeric compounds having such nucleobase sequence, whether modified or unmodified, including, but not limited to, such compounds comprising RNA bases, such as those having sequence "AUCGAUCG" and those having some DNA bases and some RNA bases such as "AUCGATCG" and oligomeric compounds having other modified or naturally occurring bases, such as "AT$^m$CGAUCG," wherein $^m$C indicates a cytosine base comprising a methyl group at the 5-position.

EXAMPLES

Example 1

Oligonucleotide Probe Design

Oligonucleotide probes were designed to be complementary to their targets, to maximize affinity to the targets, to minimize affinity to each other, and to minimize formation of secondary structure. In order to accomplish these goals, various modifications were made to the nucleobases and to the sugars. Nucleobase modifications included 5-methyl cytosine and replacing thymine with uracil. Sugar modifications included cEt, 2'-O-methoxyethyl (2'-MOE), 2'-fluoro. In some cases, a few sugars were intentionally left unmodified (2'-deoxy) in order reduce the affinity of the two probes for each other. Three to four capture probes and three to four detector probes were made to target each analyte, then all possible combinations were tested. The optimal probe combinations were determined based on low background signal, high precision across replicates, high linearity across various concentrations of analyte, and lowest lower limit of quantitation.

Example 2

General Method for Dual probeECL Oligonucleotide Detection

The analyte oligonucleotide was dissolved in PBS, then added to a biological matrix (plasma or cerebral spinal fluid, CSF) to achieve the desired dilution concentrations. 150 μL of 3% Blocker A (Meso Scale Discovery, MSD) in PBS was aliquoted into each well of an MSD standard Streptavidin coated 96-well plate (MSD) and incubated at 21° C. 1 to 2 hours while shaking at 500 rpm. Meanwhile, the desired volume of analyte-containing matrix or blank control matrix (25-50 μL) was aliquoted into each well of a separate 96-well plate. Capture probe that is labeled with biotin at the 5'-end (BioTEG from IDT) and is fully complementary to the 3'-half of the analyte oligonucleotide was added to the matrix at a final concentration of 2.5-50 nM. In order to hybridize the capture probe to the analyte, the plate was incubated 30 minutes at 65-68° C., then 30 minutes at 21° C. while shaking at 800 rpm. The Streptavidin coated plate was then washed with wash buffer (TBS/Tween 20, 0.6 M NaCl, 0.2% Tween, 50 mM Tris-HCl, pH 7.2) twice, and the hybridized capture probe—analyte samples were transferred to the Streptavidin coated plate. In order to bind the biotin-labeled duplexes to the plate, it was incubated 30 minutes at 21° C. while shaking at 500 rpm. Meanwhile, the detector probe, which is fully complementary to the 5'-half of the analyte oligonucleotide and is labeled with the electrochemiluminescent (ECL) tag tris(2,2-bipyridine) Ruthenium (II)-NHS (MSD-tag from MSD) at the 3'-end via a $C_7$-amino spacer, was heated 30 minutes in a 65° C. water bath. Next, the plate was washed twice with wash buffer, the detector probe was added at a final concentration of 1.0-2.0 nM or higher if necessary, and the plate was incubated for 1 hour at 21° C. and shaking at 500 rpm in order to hybridize the detector probe to the capture probe—analyte duplexes. The plate was then washed 4 times with wash buffer. 150 uL of read buffer T (MSD) was aliquoted into each well of the plate, and the ECL signal was read on the Sector Imager 2400 instrument (MSD) within 5 minutes of adding the read buffer according to the manufacturer's instructions. The signal was reported in relative luminescence units (RLU).

Example 3

Validation of the Dual probeECL Method in Plasma and CSF

Dilutions of ISIS 396443 (T$^m$CA$^m$CTTT$^m$CATAATG$^m$-CTGG, SEQ ID NO: 1), a uniformly 2'-methoxyethyl (2'-MOE) modified oligonucleotide with uniform phosphorothioate internucleoside linkages that targets human SMN1, were analyzed by the method described in Example 2. 25 μL of plasma or CSF was aliquoted into each well of the 96-well plate, the capture probe was added at a final concentration of 2.5 nM, and the detector probe was added at a final concentration of 1.0 nM. The capture probe, ISIS 588964 (comprising sequence: $^m$C$^m$CAG$^m$CATTA, SEQ ID NO: 2), contains 2'-modifications: keekeekee, wherein 'e' is 2'-MOE and 'k' is a cEt modification; uniform phosphodiester internucleoside linkages, and the 5'-BioTEG tag. The detector probe, ISIS 589440 (comprising sequence: TGAAAGTGA, SEQ ID NO: 3), contains 2'-modifications: kffkffkfk, wherein 'k' is a cEt modification and 'f' is 2'-fluoro; uniform phosphodiester internucleoside linkages, and the 3'-ECL tag. Five replicates of each dilution were analyzed. The results are shown in Tables 1 and 2. The "mean" column shows the average concentration of oligonucleotide determined by the assay for the five replicates. "QC" is quality control, "ULOQ" is upper limit of quantitation, and "LLOQ" is lower limit of quantitation.

TABLE 1

| | ECL method validation in plasma | | | |
| --- | --- | --- | --- | --- |
| Sample | Theoretical Concentration (ng/mL) | Mean (ng/mL) | Std Dev | Accuracy (%) |
| High QC | 7.5 | 7.32 | 0.178 | 97.6 |
| Medium QC | 1.5 | 1.40 | 0.054 | 93.3 |
| Low QC | 0.15 | 0.13 | 0.008 | 88.0 |
| ULOQ | 10 | 10.29 | 0.370 | 103 |
| LLOQ | 0.05 | 0.05 | 0.000 | 100 |

TABLE 2

ECL method validation in CSF

| Sample | Theoretical Concentration (ng/mL) | Mean (ng/mL) | Std Dev | Accuracy (%) |
|---|---|---|---|---|
| High QC | 7.5 | 7.52 | 0.135 | 100 |
| Medium QC | 1.5 | 1.40 | 0.066 | 93.6 |
| Low QC | 0.15 | 0.14 | 0.005 | 96.0 |
| ULOQ | 10 | 10.50 | 0.684 | 105 |
| LLOQ | 0.05 | 0.06 | 0.005 | 128 |

Note that in subsequent runs of the experiment, the LLOQ CSF samples achieved 97% accuracy.

Example 4

Sensitivity of the Dual Probe ECL Oligonucleotide Detection Method

Dilutions of ISIS 396443 (T$^m$CA$^m$CTTT$^m$CATAATG$^m$-CTGG, SEQ ID NO: 1) were analyzed by the method described in Examples 2 and 3. 25 µL of plasma or CSF was aliquoted into each well of the 96-well plate, the capture probe was added at a final concentration of 2.5 nM, and the detector probe was added at a final concentration of 1.0 nM. Two replicates of each dilution were analyzed. The results are shown in Tables 3 and 4 below.

The sensitivity of this new method was compared with results previously obtained with a known, state-of-the-art method. In that experiment, dilutions of ISIS 396443 were analyzed by a hybridization ELISA (described in Wei et al., Pharm. Res. 2006, 23, 1251-1264) using a single probe labeled at the 3'-end with digoxigenin and the 5'-end with biotin. The results are shown in Tables 3 and 4. The curves for both the ECL method and the hybridization ELISA (HELISA) are linear. The ECL method has an LLOQ of 0.05 ng/mL, whereas the HELISA has an LLOQ of 1 ng/mL in plasma and 2 ng/mL in CSF.

TABLE 3

Sensitivity of ECL oligonucleotide detection method vs. HELISA in plasma

| ISIS 396443 Concentration (ng/mL) | ECL Method Result (RLU) | HELISA Result (RFU) |
|---|---|---|
| 0.05 | 221.5 | n/a |
| 0.075 | 293.5 | n/a |
| 0.1 | 372.5 | n/a |
| 0.25 | 805.5 | n/a |
| 0.5 | 1612.5 | n/a |
| 1 | 2912 | 1115 |
| 2 | n/a | 1748 |
| 2.5 | 7337.5 | n/a |
| 5 | 12770 | 3085.5 |
| 8 | 21350 | n/a |
| 10 | 25825 | 5672.6 |
| 25 | n/a | 11545 |
| 50 | n/a | 20683 |
| 100 | n/a | 40394 |
| 150 | n/a | 47755 |

TABLE 4

Sensitivity of ECL oligonucleotide detection method vs. HELISA in CSF

| ISIS 396443 Concentration (ng/mL) | ECL Method Result (RLU) | HELISA Result (RFU) |
|---|---|---|
| 0.05 | 127.5 | n/a |
| 0.075 | 167 | n/a |
| 0.1 | 200.5 | n/a |
| 0.25 | 462.5 | n/a |
| 0.5 | 868 | n/a |
| 1 | 1681 | n/a |
| 2 | n/a | 1282.2 |
| 2.5 | 4397 | n/a |
| 5 | 8956.5 | 2104.9 |
| 8 | 14060 | n/a |
| 10 | 18744 | 3389.5 |
| 25 | n/a | 6262.2 |
| 50 | n/a | 11911 |
| 100 | n/a | 21155 |
| 150 | n/a | 28881 |

Example 5

Intra-Assay Accuracy and Precision

Five or six replicate samples of seven dilutions were used to evaluate intra-assay accuracy and precision in plasma and CSF. The samples were analyzed as described in examples 2 and 3 above. Accuracy was calculated as the percentage difference between the measured concentrations and the theoretical concentrations for ISIS 396443. Precision is expressed as coefficient of variation (% CV). The results are shown in Tables 5 and 6 below. Accuracy and precision are <15% and <10%, respectively, for all seven dilutions. These values are well below the acceptable limits of <25% accuracy and precision for LLOQ and <20% for all other concentrations.

TABLE 5

Intra-assay accuracy and precision in plasma

| Theoretical Concentration (ng/mL) | Mean (ng/mL) | Std Dev | % CV | % Difference between Mean and Theoretical |
|---|---|---|---|---|
| 0.0500 | 0.0565 | 0.00291 | 5.15 | 13.0 |
| 0.0750 | 0.0812 | 0.00188 | 2.31 | 8.27 |
| 0.150 | 0.153 | 0.00395 | 2.57 | 2.27 |
| 1.50 | 1.48 | 0.0322 | 2.18 | −1.58 |
| 7.50 | 7.28 | 0.552 | 7.59 | −2.99 |
| 8.00 | 8.07 | 0.210 | 2.60 | 0.914 |
| 10.0 | 11.4 | 0.215 | 1.89 | 13.6 |

TABLE 6

Intra-assay accuracy and precision in CSF

| Theoretical Concentration (ng/mL) | Mean (ng/mL) | Std Dev | % CV | % Difference between Mean and Theoretical |
|---|---|---|---|---|
| 0.0500 | 0.0485 | 0.00252 | 5.19 | −3.00 |
| 0.0750 | 0.0849 | 0.00246 | 2.90 | 13.3 |
| 0.150 | 0.152 | 0.00277 | 1.83 | 1.09 |
| 1.50 | 1.45 | 0.0465 | 3.21 | −3.39 |
| 7.50 | 7.42 | 0.233 | 3.14 | −1.06 |

TABLE 6-continued

Intra-assay accuracy and precision in CSF

| Theoretical Concentration (ng/mL) | Mean (ng/mL) | Std Dev | % CV | % Difference between Mean and Theoretical |
|---|---|---|---|---|
| 8.00 | 7.61 | 0.0690 | 0.910 | −4.82 |
| 10.0 | 8.78 | 0.248 | 2.82 | −12.2 |

Example 6

Inter-Clay Accuracy and Precision

Inter-day accuracy and precision were calculated from the pooled data of ten experiments run on separate days, for a total of 17 to 18 replicates for each dilution. Experiments were performed as described in examples 2 and 3. The results are shown in Tables 7 and 8 below. Accuracy and precision are both well below acceptable limits (see example 5), both <10% in plasma and ≤15% in CSF.

TABLE 7

Inter-day accuracy and precision in plasma

| Theoretical Concentration (ng/mL) | Mean (ng/mL) | Std Dev | % CV | % Difference between Mean and Theoretical |
|---|---|---|---|---|
| 0.0500 | 0.0514 | 0.00410 | 7.98 | 2.78 |
| 0.0750 | 0.0765 | 0.00670 | 8.77 | 1.94 |
| 0.150 | 0.160 | 0.00993 | 6.21 | 6.52 |
| 1.50 | 1.54 | 0.0982 | 6.40 | 2.37 |
| 7.50 | 7.88 | 0.524 | 6.65 | 5.09 |
| 8.00 | 8.42 | 0.594 | 7.06 | 5.30 |
| 10.0 | 10.6 | 0.628 | 5.94 | 5.78 |

TABLE 8

Inter-day accuracy and precision in CSF

| Theoretical Concentration (ng/mL) | Mean (ng/mL) | Std Dev | % CV | % Difference between Mean and Theoretical |
|---|---|---|---|---|
| 0.0500 | 0.0447 | 0.00398 | 8.90 | −10.6 |
| 0.0750 | 0.0753 | 0.0113 | 15.0 | 0.413 |
| 0.150 | 0.141 | 0.0139 | 9.85 | −6.23 |
| 1.50 | 1.38 | 0.107 | 7.71 | −7.71 |
| 7.50 | 6.99 | 0.413 | 5.91 | −6.83 |
| 8.00 | 7.68 | 0.356 | 4.63 | −3.99 |
| 10.0 | 9.43 | 0.584 | 6.20 | −5.74 |

Example 7

Evaluation of the Dual probeECL Oligonucleotide Detection Method for the Prozone Effect In order to test whether the ECL oligonucleotide detection method was subject to the prozone effect, also known as the hook effect, a 20,000 ng/mL ISIS 396443 plasma sample was serially diluted, and the dilutions were analyzed as described in examples 2 and 3. The results are shown in Table 9. While some dilutions were above the limit of quantitation ("ALOQ") of 10.0 ng/mL, no significant prozone effect was observed with any dilution tested.

TABLE 9

Test for the prozone effect

| Theoretical Dilution Concentration (ng/mL) | Dilution Factor | Mean RLU | Observed Dilution Concentration (ng/mL) | Observed Concentration Corrected by Dilution Factor (ng/mL) | % Difference between Observed and Theoretical Concentrations |
|---|---|---|---|---|---|
| 20,000 | n/a | 68,706 | ALOQ | n/a | n/a |
| 10,000 | 1:2 | 75,342 | ALOQ | n/a | n/a |
| 2,000 | 1:10 | 79,765 | ALOQ | n/a | n/a |
| 400 | 1:50 | 77,247 | ALOQ | n/a | n/a |
| 40.0 | 1:500 | 71,155 | ALOQ | n/a | n/a |
| 8.00 | 1:2,500 | 14,888 | 7.86 | 19,650 | −1.75 |
| 4.00 | 1:5,000 | 7,461 | 3.74 | 18,700 | −6.50 |
| 0.80 | 1:25,000 | 1,527 | 0.68 | 17,000 | −15.0 |

Example 8

Dilution Linearity of the Dual Probe ECL Oligonucleotide Detection Method

In order to determine the linear dilution range of the ECL oligonucleotide detection method, 250-4000 fold dilutions of ISIS 396443 in plasma and CSF were made, and three replicates of each dilution were analyzed as described in examples 2 and 3. The results are shown in Table 10. All of the dilutions surpassed acceptable criteria for precision (<15%) and accuracy (<15%); thus the ECL method has a linear dilution range of 0.05 ng/mL (the LLOQ) up to at least 40,000 ng/mL (the ULOQ multiplied by 4000).

TABLE 10

Dilution linearity of the ECL oligonucleotide detection method in plasma and CSF

| Dilution | Theoretical Concentration (ng/mL) | Observed Concentration (ng/mL) | Std Dev | % CV | % Difference from Theoretical |
|---|---|---|---|---|---|
| 250-fold plasma | 1000 | 1080 | 33.8 | 3.14 | 7.66 |
| 1000-fold plasma | 1000 | 1060 | 30.1 | 2.83 | 6.27 |
| 4000-fold plasma | 1000 | 1080 | 89.0 | 8.21 | 8.38 |
| 250-fold CSF | 1000 | 878 | 35.9 | 4.09 | −12.2 |
| 1000-fold CSF | 1000 | 1000 | 112 | 11.1 | 0.200 |
| 4000-fold CSF | 1000 | 1060 | 108 | 10.1 | 6.40 |

Example 9

Detection of Structured Oligonucleotides with the Dual Probe ECL Method

Certain oligonucleotide sequences form structures that are difficult to detect or quantitate with the HELISA method that utilizes a single probe. Each of the two ECL "halfmer" probes is less prone to secondary structure formation, and 2'-sugar modifications of the halfmer probes were optimized to maximize affinity to the target oligonucleotide and minimize secondary structure formation. To test the prediction that the ECL method can detect difficult sequences that the HELISA cannot detect, oligonucleotide ISIS 440762 (T$^m$-CAGT$^m$CATGA$^m$CTT$^m$C, SEQ ID NO: 4), containing 10 consecutive nucleotides that are self-complementary, was used as the analyte. ISIS 440762 is a 2-10-2 gapmer with cEt modified wings, a 2'-deoxy gap, and uniform phosphorothioate internucleoside linkages that targets mouse SCARB1. It was added to plasma and analyzed by the method described in Example 2. 50 μL of plasma was aliquoted into each well of the 96-well plate, the capture probe was added at a final concentration of 50 nM, and the detector probe was added at a final concentration of 1.5 nM. The capture probe, ISIS 632043 (comprising sequence: GAAGT$^m$CA, SEQ ID NO: 5), contains 2'-modifications: kkeekke, wherein 'e' is 2'-MOE and 'k' is a cEt modification; uniform phosphodiester internucleoside linkages, and the 5'-BioTEG tag. The detector probe, ISIS 632044 (comprising sequence: TGA$^m$-CTGA, SEQ ID NO: 6), contains 2'-modifications: kdedkfe, wherein 'k' is a cEt modification, 'd' is 2'-deoxy, 'e' is 2'-MOE, and 'f' is 2'-fluoro; uniform phosphodiester internucleoside linkages, and the 3'-ECL tag. Two replicates of each dilution were analyzed. The results are shown in Table 11 and shown along with the results using the HELISA method to detect the same analyte, ISIS 440762. While the RFU signal from the HELISA is background, the ECL method results give a linear curve, indicating that the analyte is detectable and successfully quantitated with the ECL method.

TABLE 11

Detection of a structured oligonucleotide using the ECl method vs. the HELISA

| ISIS 440762 Concentration (ng/mL) | ECL Method Result (RLU) | HELISA Result (RFU) |
|---|---|---|
| 0.5 | n/a | 1000.931 |
| 1 | n/a | 963.646 |
| 2 | 231.5 | 997.105 |
| 5 | 475.0 | 1040.123 |
| 10 | 864.0 | 940.771 |
| 25 | 2222.5 | 1019.817 |
| 50 | 4284.5 | 933.808 |
| 100 | 8997.5 | 868.686 |
| 150 | n/a | 788.130 |
| 200 | 14108.0 | 918.982 |
| 300 | 20147.5 | n/a |

Example 10

Intra-Assay Accuracy and Precision Using a Structured Analyte Oligonucleotide

Three to five replicate samples of five dilutions were used to evaluate intra-assay accuracy and precision in plasma using structured analyte ISIS 440762. The samples were analyzed as described in examples 2 and 9 above. Accuracy was calculated as the percentage difference between the measured concentrations and the theoretical concentrations for ISIS 440762. Precision is expressed as coefficient of variation (% CV). The results are shown in Table 12. Accuracy and precision are both acceptable (<15%) for most dilutions. The accuracy of >20% for the 2,000 ng/mL sample indicates that the method is not quite as robust for this difficult to detect, structured oligonucleotide analyte as it is for unstructured analytes, but these results demonstrate that it is a reliable and sensitive method that far exceeds the capability of the state-of-the-art HELISA method.

TABLE 12

Intra-assay accuracy and precision in plasma using a structured analyte

| Theoretical Concentration (ng/mL) | Mean (ng/mL) | Std Dev | % CV | % Difference between Mean and Theoretical |
|---|---|---|---|---|
| 2.000 | 2.414 | 0.168 | 6.979 | 20.680 |
| 6.000 | 6.653 | 0.324 | 4.871 | 10.891 |
| 75.000 | 74.043 | 7.153 | 9.661 | −1.277 |
| 250.000 | 247.334 | 22.358 | 9.040 | −1.066 |
| 300.000 | 304.131 | 22.706 | 7.466 | 1.377 |

Example 11

Use of the Dual probeECL Method to Detect a MOE Gapmer Oligonucleotide

Dilutions of ISIS 449884 (GGTT$^m$C$^m$C$^m$CGAGGT G$^m$C$^m$C$^m$CA, SEQ ID NO: 7), a 3-10-4 MOE gapmer with 2'-MOE modified wings, a 2'-deoxy gap, and uniform phosphorothioate internucleoside linkages that targets human glucagon receptor, were analyzed by the method described in Example 2. 25 µL of plasma spiked with ISIS 449884 was aliquoted into each well of the 96-well plate, the capture probe was added at a final concentration of 25 nM, and the detector probe was added at a final concentration of 10 nM. The capture probe, ISIS 690416 (comprising sequence: TGIG$^m$CA$^m$C$^m$C, SEQ ID NO: 8), wherein I is inosine, contains 2'-modifications: ekdeekee, wherein 'e' is 2'-MOE and 'k' is a cEt modification; uniform phosphodiester internucleoside linkages, and the 5'-BioTEG tag. The detector probe, ISIS 589440 (comprising sequence: TGAAAGTGA, SEQ ID NO: 3), contains 2'-modifications: kffkffkfk, wherein 'k' is a cEt modification and 'f' is 2'-fluoro; uniform phosphodiester internucleoside linkages, and the 3'-ECL tag. Six replicates of each dilution were analyzed. The results are shown in Table 13. The "mean" column shows the average concentration of oligonucleotide determined by the assay for the six replicates. "QC" is quality control, "ULOQ" is upper limit of quantitation, and "LLOQ" is lower limit of quantitation.

TABLE 13

Dual probe ECL detection of a MOE gapmer

| Sample | Theoretical Concentration (ng/mL) | Mean (ng/mL) | Std Dev | Accuracy (%) |
|---|---|---|---|---|
| High QC | 150.00 | 161.72 | 3.76 | 108 |
| Medium QC | 20.00 | 20.22 | 0.54 | 101 |
| Low QC | 0.75 | 0.64 | 0.02 | 85 |
| ULOQ | 200.00 | 219.55 | 7.57 | 110 |
| LLOQ | 0.25 | 0.25 | 0.02 | 100 |

Example 12

Dilution Linearity of the Dual Probe ECL Oligonucleotide Detection of a MOE Gapmer Dilutions of ISIS 449884 in plasma were made, and replicates of each dilution were analyzed as described in example 11. The results are shown in Table 14. The R squared value for the curve of the theoretical concentration vs observed mean concentration is 0.999, indicating excellent linearity from 0.25-200 ng/mL.

TABLE 14

Dilution linearity of the ECL oligonucleotide detection method of a MOE gapmer

| Theoretical Concentration (ng/mL) | Mean (ng/mL) | % CV | % Difference between Mean and Theoretical |
|---|---|---|---|
| 0.25 | 0.28 | 1.7 | 12.0 |
| 0.50 | 0.51 | 6.6 | 2.0 |
| 1.00 | 0.92 | 3.1 | −8.0 |
| 2.00 | 1.94 | 5.6 | −3.0 |
| 5.00 | 4.83 | 1.2 | −3.4 |
| 10.00 | 9.73 | 0.3 | −2.7 |
| 25.0 | 23.8 | 1.8 | −4.8 |
| 50.0 | 50.75 | 8.5 | 1.5 |
| 100.0 | 107.03 | 7.0 | 7.0 |
| 200.0 | 203.33 | 0.4 | 1.7 |

Example 13

Optimization of Detection Method to Eliminate Interference from Antibodies

When oligonucleotides are administered in vivo, antibodies that bind the oligonucleotide may form. Such antibodies may interfere with oligonucleotide detection by reducing binding of the probes to the oligonucleotide analyte. In order to prevent antibodies from interfering with oligonucleotide detection, detection of ISIS 449884 was performed similarly as described in Example 11, with the addition of Proteinase K along with the capture probe, and changes to the capture probe incubation temperatures and times. Antibodies against ISIS 449884 were raised in rabbits and added to some samples to test whether interference conferred by the antibodies is abrogated by Proteinase K. The results in Table 15 show that the presence of the antibody interfered with detection of the oligonucleotide, and addition of Proteinase K under certain conditions completely restored detection of the oligonucleotide analyte. The optimal conditions for ISIS 449884 detection were 5 units/mL ("U/mL") of Proteinase K, and incubations at 45° C. for 90 minutes, 80° C. for 30 minutes, and 21° C. for 30 minutes.

TABLE 15

Optimization of Proteinase K incubation to eliminate antibody interference

| Proteinase K (U/mL) | Incubations (° C./min) | Antibody added (µg/mL) | Theoretical ISIS 449884 conc. (ng/mL) | Observed conc. (ng/mL) | % Recovery (relative to theoretical conc.) |
|---|---|---|---|---|---|
| 0 | 68/30, 21/30 | 10 | 25 | 1.06 | 4.24 |
| 0 | 68/30, 21/30 | 0 | 25 | 24.21 | 96.84 |
| 0 | 68/30, 21/30 | 10 | 3 | 0.07 | 2.33 |
| 0 | 68/30, 21/30 | 0 | 3 | 2.81 | 93.67 |
| 0 | 68/30, 21/30 | 10 | 1 | 0.03 | 3.00 |
| 0 | 68/30, 21/30 | 0 | 1 | 1.00 | 100.00 |
| 5 | 45/60, 75/60, 21/30 | 10 | 25 | 11.7 | 46.80 |
| 5 | 45/60, 75/60, 21/30 | 0 | 25 | 14.56 | 58.24 |

TABLE 15-continued

Optimization of Proteinase K incubation to eliminate antibody interference

| Proteinase K (U/mL) | Incubations (° C./min) | Antibody added (μg/mL) | Theoretical ISIS 449884 conc. (ng/mL) | Observed conc. (ng/mL) | % Recovery (relative to theoretical conc.) |
|---|---|---|---|---|---|
| 5 | 45/60, 75/60, 21/30 | 10 | 3 | 1.33 | 44.33 |
| 5 | 45/60, 75/60, 21/30 | 0 | 3 | 1.75 | 58.33 |
| 5 | 45/60, 75/60, 21/30 | 10 | 1 | 0.46 | 46.00 |
| 5 | 45/60, 75/60, 21/30 | 0 | 1 | 0.76 | 76.00 |
| 10 | 45/60, 75/60, 21/30 | 10 | 25 | 12.33 | 49.32 |
| 10 | 45/60, 75/60, 21/30 | 0 | 25 | 13.64 | 54.56 |
| 10 | 45/60, 75/60, 21/30 | 10 | 3 | 1.36 | 45.33 |
| 10 | 45/60, 75/60, 21/30 | 0 | 3 | 1.68 | 56.00 |
| 10 | 45/60, 75/60, 21/30 | 10 | 1 | 0.46 | 46.00 |
| 10 | 45/60, 75/60, 21/30 | 0 | 1 | 0.64 | 64.00 |
| 5 | 45/60, 75/90 | 10 | 25 | 8.84 | 35.36 |
| 5 | 45/60, 75/90 | 0 | 25 | 15.24 | 60.96 |
| 5 | 45/60, 75/90 | 10 | 3 | 0.82 | 27.33 |
| 5 | 45/60, 75/90 | 0 | 3 | 1.75 | 58.33 |
| 5 | 45/60, 75/90 | 10 | 1 | 0.29 | 29.00 |
| 5 | 45/60, 75/90 | 0 | 1 | 0.58 | 58.00 |
| 10 | 45/60, 75/90 | 10 | 25 | 9.53 | 38.12 |
| 10 | 45/60, 75/90 | 0 | 25 | 14.93 | 59.72 |
| 10 | 45/60, 75/90 | 10 | 3 | 0.85 | 28.33 |
| 10 | 45/60, 75/90 | 0 | 3 | 1.52 | 50.67 |
| 10 | 45/60, 75/90 | 10 | 1 | 0.29 | 29.00 |
| 10 | 45/60, 75/90 | 0 | 1 | 0.67 | 67.00 |
| 5 | 45/90, 80/30, 21/30 | 10 | 25 | 22.5 | 89.94 |
| 5 | 45/90, 80/30, 21/30 | 0 | 25 | 21.9 | 87.64 |
| 5 | 45/90, 80/30, 21/30 | 10 | 3 | 2.75 | 91.33 |
| 5 | 45/90, 80/30, 21/30 | 0 | 3 | 2.65 | 88.00 |
| 5 | 45/90, 80/30, 21/30 | 10 | 1 | 1.05 | 105.00 |
| 5 | 45/90, 80/30, 21/30 | 0 | 1 | 1.0 | 99.50 |
| 5 | 45/120, 80/30, 21/30 | 10 | 25 | 21.4 | 85.48 |
| 5 | 45/120, 80/30, 21/30 | 0 | 25 | 27.65 | 110.60 |
| 5 | 45/120, 80/30, 21/30 | 10 | 3 | 2.25 | 75.00 |
| 5 | 45/120, 80/30, 21/30 | 0 | 3 | 3.05 | 101.33 |
| 5 | 45/120, 80/30, 21/30 | 10 | 1 | 0.9 | 89.50 |
| 5 | 45/120, 80/30, 21/30 | 0 | 1 | 1.05 | 106.50 |

Example 14

Dilution Linearity of the Dual Probe ECL Method with Proteinase K Digestion

Dilutions of ISIS 449884 in plasma were made, and replicates of each dilution were analyzed as described in example 13 using the optimized incubation conditions for the Proteinase K and capture probe addition to the sample. The results are shown in Table 16 and indicate that the dual probe ECL method with Proteinase K digestion provided accurate detection of an oligonucleotide analyte in the presence of antibody over a range of concentrations.

TABLE 16

Dilution linearity of the ECL oligonucleotide detection method of a MOE gapmer

| Antibody added (μg/mL) | Theoretical Concentration (ng/mL) | Mean (ng/mL) | % Difference between Mean and Theoretical |
|---|---|---|---|
| 10 | 200 | 230.24 | 115.12 |
| 0 | 200 | 226.16 | 113.08 |
| 10 | 150 | 173.31 | 115.54 |
| 0 | 150 | 167.71 | 109.80 |
| 10 | 25 | 21.17 | 84.66 |
| 0 | 25 | 22.77 | 91.06 |
| 10 | 3 | 2.69 | 89.54 |
| 0 | 3 | 2.58 | 86.08 |
| 10 | 1 | 0.81 | 81.13 |
| 0 | 1 | 0.85 | 85.00 |

We claim:

1. A method for detecting or quantitating a target oligonucleotide in a bodily fluid or extract, wherein the target oligonucleotide is 14 to 50 nucleosides in length and comprises at least one modified nucleoside, comprising:
forming a test sample by contacting the bodily fluid or extract with a capture probe, wherein:
the capture probe is complementary to a first portion of the target oligonucleotide; and
the capture probe comprises a binding moiety, wherein the binding moiety is covalently bound to the capture probe; and
the capture probe comprises at least five modified nucleosides, wherein each modified nucleoside comprises a modified sugar moiety;
contacting the test sample with a binding partner of the binding moiety of the capture probe, wherein the binding partner is attached to a solid support;
contacting the test sample with a detector probe, wherein:
the detector probe is complementary to a second portion of the target oligonucleotide, wherein the first portion and the second portion of the target oligonucleotide do not overlap; and
the detector probe comprises an electrochemiluminescent moiety, wherein the electrochemiluminescent moiety is covalently bound to the detector probe; and
the detector probe comprises at least five modified nucleosides, wherein each modified nucleoside comprises a modified sugar moiety;
washing the test sample to remove unbound detector probe;
detecting the presence or amount of the electrochemiluminescent moiety of the detector probe hybridized to the target oligonucleotide; and
thereby detecting or quantitating the target oligonucleotide in the bodily fluid or extract.

2. The method of claim 1, wherein the target oligonucleotide is 14-22 nucleosides in length.

3. The method of claim 1, wherein the target oligonucleotide is an antisense oligonucleotide.

4. The method of claim 1, wherein the bodily fluid is plasma.

5. The method of claim 1, wherein the bodily fluid is cerebral-spinal fluid.

6. The method of claim 1, wherein the method does not comprise addition of a ligase.

7. The method of claim 1, wherein the method is performed using less than 100 µL of biological fluid or extract.

8. The method of claim 1, comprising administering the target oligonucleotide to an animal and collecting the bodily fluid or extract.

9. The method of claim 1, wherein the detector probe is heated prior to contacting the test sample with the detector probe.

10. The method of claim 1, comprising contacting the test sample with a protease.

11. The method of claim 1, wherein the detector probe and the capture probe are each 7 to 10 nucleotides in length.

12. The method of claim 1, wherein the target oligonucleotide comprises a conjugate group.

13. The method of claim 1, wherein the method has a sensitivity of less than 500 pg/mL of target oligonucleotide.

14. The method of claim 1, wherein the capture probe comprises at least one modified nucleoside comprising a bicyclic sugar moiety comprising a 4'-CH(CH$_3$)—O-2' bridge, and at least one modified nucleoside comprising a 2'-O-methoxyethyl sugar modification.

15. The method of claim 1, wherein detector probe comprises at least one modified nucleoside comprising a bicyclic sugar moiety comprising a 4'-CH(CH$_3$)—O-2' bridge, and at least one modified nucleoside comprising a 2'-F sugar modification.

16. The method of claim 15, wherein the capture probe comprises at least one modified nucleoside comprising a bicyclic sugar moiety comprising a 4'-CH(CH$_3$)—O-2' bridge, and at least one modified nucleoside comprising a 2'-O-methoxyethyl sugar modification.

17. The method of claim 1, wherein each modified nucleoside of the capture probe and detector probe is independently selected from a modified nucleoside comprising a bicyclic sugar moiety comprising a 4'—CH(CH$_3$)—O-2' bridge, a modified nucleoside comprising a bicyclic sugar moiety comprising a 4'-CH$_2$—O-2'bridge, a modified nucleoside comprising a 2'-O-methoxyethyl sugar modification, a modified nucleoside comprising a 2'-O-methyl sugar modification, and a modified nucleoside comprising a 2'-F sugar modification.

18. The method of claim 1, wherein the electrochemiluminescent moiety is a tris(2,2-bipyridine) Ruthenium (II) complex.

19. The method of claim 16, wherein the detector probe and the capture probe are each 7 to 10 nucleotides in length.

20. The method of claim 19, wherein the electrochemiluminescent moiety is a tris(2,2-bipyridine) Ruthenium (II) complex.

21. The method of claim 17, wherein the detector probe and the capture probe are each 7 to 10 nucleotides in length.

22. The method of claim 21, wherein the electrochemiluminescent moiety is a tris(2,2-bipyridine) Ruthenium (II) complex.

* * * * *